US009775913B2

(12) United States Patent
Lauermann

(10) Patent No.: US 9,775,913 B2
(45) Date of Patent: Oct. 3, 2017

(54) METHOD OF SITE SPECIFIC ACTIVATION OF AN ANTIBODY BY A PROTEASE

(71) Applicant: Vit Lauermann, Belmont, CA (US)

(72) Inventor: Vit Lauermann, Belmont, CA (US)

( * ) Notice: Subject to any disclaimer, the term of this patent is extended or adjusted under 35 U.S.C. 154(b) by 0 days.

(21) Appl. No.: 14/226,324

(22) Filed: Mar. 26, 2014

(65) Prior Publication Data

US 2015/0314014 A1 Nov. 5, 2015

Related U.S. Application Data

(62) Division of application No. 10/651,584, filed on Aug. 30, 2003, now Pat. No. 8,809,504.

(51) Int. Cl.
| | |
|---|---|
| *C12P 21/08* | (2006.01) |
| *A61K 47/48* | (2006.01) |
| *C07K 14/705* | (2006.01) |
| *C07K 16/24* | (2006.01) |
| *C07K 16/40* | (2006.01) |
| *A61K 38/20* | (2006.01) |
| *C07K 14/47* | (2006.01) |
| *A61K 39/00* | (2006.01) |
| *A61K 38/00* | (2006.01) |

(52) U.S. Cl.
CPC .... *A61K 47/48338* (2013.01); *A61K 38/2013* (2013.01); *C07K 14/4703* (2013.01); *C07K 14/70575* (2013.01); *C07K 14/70578* (2013.01); *C07K 16/246* (2013.01); *C07K 16/40* (2013.01); *A61K 38/00* (2013.01); *A61K 2039/505* (2013.01); *C07K 2317/76* (2013.01)

(58) Field of Classification Search
CPC .......................... A61K 47/48338; C07K 16/40
See application file for complete search history.

(56) References Cited

U.S. PATENT DOCUMENTS 6,093,399 A * 7/2000 Thorpe ............ A61K 47/48561 424/178.1
6,368,598 B1 * 4/2002 D'Amico ............... A61K 38/06 424/179.1
7,091,321 B2 * 8/2006 Gillies ............. A61K 47/48423 424/134.1

OTHER PUBLICATIONS

Mhaka et al., Bioorg. Med. Chem. Letters 12: 2459-2461, 2002.*

* cited by examiner

*Primary Examiner* — Gyan Chandra

(57) ABSTRACT

The invention relates to molecules inhibiting biologically active compounds and further comprising moieties specifically cleavable by a reagent produced by a target cell. More specifically, the invention relates to inhibitors that bind, inhibit, suppress, neutralize, or decrease activity of a biologically active agent. Inhibitors comprise at least one moiety that bind, inhibit, suppress, neutralize, or decrease activity of a biologically active agent and at least one moiety that can be cleaved specifically by a reagent produced by target cells. The cleavage deactivates the inhibitor. Following cleavage, the active agent is liberated into the local environment. Administration of the inhibitor alone or together with the active agent suppress the compound's activity until it reaches the proximity of a target cell. This targeted specific release enables the agent concentration in a site to reach levels that have desired therapeutic effects without systemic toxicity. The invention also relates to production and uses of the inhibitors in diagnosis and treatment of a disease.

22 Claims, No Drawings

METHOD OF SITE SPECIFIC ACTIVATION OF AN ANTIBODY BY A PROTEASE

CROSS-REFERENCE TO RELATED APPLICATIONS

The present application claims priority of U.S. Provisional Patent Application No. 60/407,471 filed Sep. 3, 2002. The disclosure of which is incorporated herein by reference in its entirety and for all purposes.

FIELD OF INVENTION

The invention relates to inhibitors that are useful for diagnosing and treating a disease. The invention further relates to diagnosis and treatment of a disease using biologically active molecules.

BACKGROUND OF THE INVENTION

The present invention relates to an inhibitor that can be deactivated by a reagent produced by a target cell and to its preparation and use. The inhibitor can be administered alone or together with an active agent such that the activity or toxicity of the active agent is reduced until it reaches a target cell producing a reagent wherein the inhibitor is cleaved by said reagent. Specific cleavage of the inhibitor causes inhibitory activity reduction of the inhibitor and as a consequence activity of the active agent is restored.

In order to improve therapeutic efficacy, the local concentration of biologically active agents in a disease site has to be increased without causing severe side effects. One way to decrease toxicity is to inject low doses of an active agent that are effective against cancer directly to tumor. The introduction of cytokine genes into tumor cells and subsequent local secretion can also circumvent the systemic cytokine toxicity. Local production of cytokines by genetically engineered tumor cells decreases their tumorigenicity and elicits protective immune responses against the parental tumor cells. An alternative approach to generate high local concentrations of cytokines in the tumor microenvironment is to use fusion proteins. Cytokine can also be delivered to target tumor cells using tumor specific antibodies. Effective local cytokine concentrations can be achieved at tumor sites. Immunoglobulin and cytokine can be fused into one protein molecule. The engineered antibody-cytokine fusion proteins combine the targeting ability of tumor-specific antibody with the activity of cytokines. These fusion proteins target cytokine to tumors, stimulate immune destruction of tumors and limit severe toxic side-effects of high dose cytokine administration. Monoclonal antibodies can specifically bind to a receptor or other target on the surface of disease cells and produce a desired therapeutic effect. These surface proteins are usually overexpressed on cancer cells and also expressed, to some degree, on normal cells. Such expression pattern creates difficulties in the tumor-selective antibody delivery and decreases specificity of the therapy. Higher amounts of antibodies are required to achieve the desired effects and result in increased side effects and higher cost of treatment.

Angiogenesis and cancer invasion are linked to the overexpression of proteases namely matrix metalloproteinases (MMPs) and prostate specific antigen (PSA). Matrix metalloproteinases belong to the group of endogenous proteases which are able to degrade various components of extracellular matrix, such as collagen, elastin and gelatin. A positive correlation between MMP expression and increased invasiveness and progression has been demonstrated in a wide range of human cancers including breast, colon, lung and prostate. The tumor-associated serine protease plasmin, its activator uPA (urokinase-type plasminogen activator), the receptor uPA-R (CD87), and the inhibitors PAI-1 and PAI-2 are linked to cancer invasion and metastasis as well. In cancer, increase of uPA, uPA-R, and/or PAI-1 is associated with tumor progression and with shortened disease-free and/or overall survival in patients afflicted with malignant solid tumors.

The cancer-specific proteases have been used to activate anti-cancer compounds at the tumor site. Staphylococcal toxin was constructed by fusion with a peptide that inactivated the protein. This constructs was highly susceptible to peptide cleavage by cathepsin B, a protease secreted by certain metastatic tumor cells. The toxin obtained by this cleavage was rendered active and permeabilized specifically malignant cells [Panchal, 1996].

Target-specific retroviral vectors have been developed that use the cancer-specific proteases for their activation. Retroviral vectors for selective gene delivery were targeted to matrix metalloprotease expressing cells. Infectivity of viral vector was blocked by a polypeptide fused to the viral envelope glycoprotein. In the presence of exogenous MMPs produced by target cells, the envelope function was restored when a protease cleaved the connecting linker, releasing the inhibitory polypeptide from the viral surface. Protease specificity was achieved by engineering the sequence of the linker. In vivo, the targeted vectors showed strong selectivity for matrix metalloprotease-rich tumor xenografts [Peng, 1997; Peng, 1999]. A single-chain variable fragment antibody (scFv) directed against the surface melanoma glycoprotein was fused to the amphotropic murine leukemia virus envelope to target this retroviruses specifically to melanomas. A peptide containing matrix metalloprotease (MMP) cleavage site linked the antibody with the envelope. Following virus attachment to target cell, MMP cleaved the peptide, the antibody was removed and allowed virus infection. This approach produced efficient, targeted retroviruses suitable for in vivo gene delivery [Martin, 1999; Martin, 2002]. A strategy to target cytotoxic agents specifically to sites of metastatic cancer that secretes proteases has been developed. Doxorubicin was linked to the carrier peptide moiety substantially inhibiting the non-specific toxicity of the drug. The carrier, PSA-specific peptide, determines target specificity of the drug. The drug becomes activated when processed proteolytically within prostate cancer metastases by prostate-specific antigen. PSA, which is secreted by prostatic glandular cells cleaves specifically the peptide part of the prodrug activating the therapeutic drugs and exerting their toxicity. This strategy can be used to deliver higher intratumoral levels of doxorubicin [Denmeade, 1998; DeFeo-Jones, 2000; Khan, 2000; Denmeade, 2001; Wong, 2001; DiPaola, 2002; Jones, 2002; Mhaka, 2002].

U.S. Pat. No. 6,080,575 discloses a substance which is activated by an enzyme which is released from mammalian cells.

U.S. Pat. No. 6,593,132 discloses a protein having an A chain of a ricin-like toxin, a B chain of a ricin like toxin and a heterologous linker amino acid sequence, linking the A and B chains.

U.S. Pat. No. 6,423,513 discloses a protease-activatable *Pseudomonas* exotoxin A-like proproteins and methods of using these proproteins for killing target cells.

U.S. Pat. No. 5,599,686 discloses oligopeptides which comprise amino acid sequences that are recognized and proteolytically cleaved by free prostate specific antigen.

U.S. Pat. No. 5,976,535 discloses pretargeting protocols for the enhanced localization of cytotoxins to target sites and cytotoxic combinations. The application teaches targeting of cytotoxins using biotin-streptavidin conjugates.

U.S. Pat. No. 6,036,955 discloses specific in vivo coagulation of tumor vasculature, causing tumor regression, through the site-specific delivery of a coagulant using a bispecific antibody.

U.S. Pat. No. 5,098,702 discloses administration to the mammalian host a synergistically effective amount of TNF and IL-2 or of TNF and IFN-beta, or of TNF, IL-2 and IFN-beta in combination.

U.S. Pat. No. 5,078,996 discloses a treatment by direct administration of therapeutically effective quantities of activated granulocyte-macrophage colony stimulating factor.

U.S. Pat. No. 5,447,851 discloses a specifically cleavable linker peptide functionally interposed between the cytokine receptor polypeptide and the IgG heavy chain polypeptide. Such a linker peptide provides by its inclusion in the chimeric construct, a site within the resulting chimeric polypeptide which may be cleaved in a manner to separate the active cytokine receptor polypeptide from the intact IgG heavy chain polypeptide.

U.S. Pat. No. 5,856,456 discloses a peptide linker useful for connecting polypeptide constituents into a novel linked fusion polypeptide.

DeFeo-Jones, D., Garsky, V. M., Wong, B., Feng, D. M., Bolyar, T., Haskell, K., Kiefer, D. M., Leander, K., McAvoy, E., Lumma, P., Wai, J., Senderak, E. T., Motzel, S. L., Keenan, K., Van Zwieten, M., Lin, J. H., Freidinger, R., Huff, J., Oliff, A. and Jones, R. E. (2000) A peptide-doxorubicin 'prodrug' activated by prostate-specific antigen selectively kills prostate tumor cells positive for prostate-specific antigen in vivo. *Nat Med*, 6, 1248-1252.

Denmeade, S. R., Nagy, A., Gao, J., Lilja, H., Schally, A. V. and Isaacs, J. T. (1998) Enzymatic activation of a doxorubicin-peptide prodrug by prostate-specific antigen. *Cancer Res*, 58, 2537-2540.

Denmeade, S. R., Sokoll, L. J., Chan, D. W., Khan, S. R. and Isaacs, J. T. (2001) Concentration of enzymatically active prostate-specific antigen (PSA) in the extracellular fluid of primary human prostate cancers and human prostate cancer xenograft models. *Prostate*, 48, 1-6.

DiPaola, R., Rinehart, J., Nemunaitis, J., Ebbinghaus, S., Rubin, E., Capanna, T., Ciardella, M., Doyle Lindrud, S., Goodwin, S., Fontaine, M., Adams, N., Williams, A., Schwartz, M., Winchell, G., Wickersham, K., Deutsch, P. and Yao, S. L. (2002) Characterization of a novel prostate-specific antigen-activated peptide-doxorubicin conjugate in patients with prostate cancer. *J Clin Oncol*, 20, 1874-1879.

Jones, G. B., Mitchell, M. O., Weinberg, J. S., D'Amico, A. V. and Bubley, G. J. (2002) Towards enzyme activated antiprostatic agents. *Bioorg Med Chem Lett*, 10, 1987-1989.

Khan, S. R. and Denmeade, S. R. (2000) In vivo activity of a PSA-activated doxorubicin prodrug against PSA-producing human prostate cancer xenografts. *Prostate*, 45, 80-83.

Martin, F., Chowdhury, S., Neil, S., Phillipps, N. and Collins, M. K. (2002) Envelope-targeted retrovirus vectors transduce melanoma xenografts but not spleen or liver. *Mol Ther*, 5, 269-274.

Martin, F., Neil, S., Kupsch, J., Maurice, M., Cosset, F. L. and Collins, M. (1999) Retrovirus Targeting by Tropism Restriction to Melanoma Cells. *J Virol*, 73, 6923-6929.

Mhaka, A., Denmeade, S., Yao, W., Isaacs, J. and Khan, S. (2002) A 5-fluorodeoxyuridine prodrug as targeted therapy for prostate cancer. *Bioorg Med Chem Lett*, 12, 2459.

Panchal, R. G., Cusack, E., Cheley, S. and Bayley, H. (1996) Tumor protease-activated, pore-forming toxins from a combinatorial library. *Nat Biotechnol*, 14, 852-856.

Park, S. H. and Raines, R. T. (2000) Genetic selection for dissociative inhibitors of designated protein-protein interactions. *Nature Biotechnology*, 18, 847-851.

Peng, K. W., Morling, F. J., Cosset, F. L., Murphy, G. and Russell, S. J. (1997) A gene delivery system activatable by disease-associated matrix metalloproteinases. *Hum Gene Ther*, 8, 729-738.

Peng, K. W., Vile, R., Cosset, F. L. and Russell, S. (1999) Selective transduction of protease-rich tumors by matrix-metalloproteinase-targeted retroviral vectors. *Gene Ther*, 6, 1552-1557.

Wong, B. K., DeFeo-Jones, D., Jones, R. E., Garsky, V. M., Feng, D. M., Oliff, A., Chiba, M., Ellis, J. D. and Lin, J. H. (2001) PSA-specific and non-PSA-specific conversion of a PSA-targeted peptide conjugate of doxorubicin to its active metabolites. *Drug Metab Dispos*, 29, 313-318.

SUMMARY OF THE INVENTION

In spite of attempts in the prior art to develop inhibitors of biologically active molecules that are able to: 1) neutralize undesirable effect of an active agent or a therapeutic molecule; 2) deliver the agent or molecule to a site of a disease, and 3) release the agent or molecule in active form specifically in the target site, until the present invention such technology reminded elusive.

Recent advances in molecular biology have established functions of many biologically active molecules (such as therapeutic antibodies and cytokines) and the mechanisms of their effects in biological therapies. Availability of biologically active molecules in large amounts due to advances in recombinant technology makes their clinical use possible. However, administration of effective concentrations of many biologically active molecules for long periods is undesirable due to systemic side effects and/or toxicity such as hypotension, abnormalities in liver function, leukopenia, chill and thrombus formation. It is the object of the present invention to disclose inhibitors that bind and neutralize biologically active agents and can be deactivated by an enzyme produced by vertebrate cells. The disclosed inhibitors can be used for treatment of a disease such as cancer, inflammatory, or an autoimmune disease. The instant invention relates to a new strategy to target active agents specifically to the site of a disease. The disclosed inhibitors suppress the biological activity of administered agents, which might have undesirable systemic effects, until they are in the proximity of a target cell. At the disease site, the inhibitor is inactivated by an enzyme or reagent secreted by diseased cells and the agents are released in an active form. This specific release makes agent's concentrations at a disease site reach levels that have desired therapeutic effects. This strategy can be used to deliver high levels of agents such as cytokines, chemokines, antibodies, and other molecules, which can modulate the host's response to a disease. The immune system can be stimulated eliciting systemic responses, which can, for instance, result in immune destruction of tumors and their metastasis. The immune system can also be controlled by this treatment. For example, downregulation of immune responses benefits treatment of autoimmune diseases. The inhibitors contain one or more moieties, for example oligopeptides, that can be cleaved specifically by a reagent produced by vertebrate cells. Ideally, the binding, neutralizing, suppressing, or inhibiting activity of the inhibitor (when the oligopeptide containing the enzyme cleavage site is incorporated into the inhibitor and is intact) is the same, slightly reduced or increased compared to the unmodified inhibitor (such as, but not limiting to a soluble receptor or antibody). Also ideally, the neutralizing or inhibiting activity of the inhibitor is greatly reduced or absent upon proteolytic cleavage of the attached oligopeptide encoding the cleavage site. Also ideally, the activity of the ligand (active agent) increases significantly or returns to the activity of the unbound ligand upon cleavage of the inhibitor. While it is not necessary for practicing this aspect of the invention, the most preferred embodiment of this aspect of the invention is an inhibitor oligopeptide chimera wherein the oligopeptide in the inhibitor is cleaved by the proteolytic activity of a protease or any other native proteolytic enzymes present in the disease tissue proximity, thereby releasing the active compound, which was bond by the inhibitor, into the physiological environment at the place of the proteolytic cleavage. Tumors as well as inflamed areas are distinguished from the surrounding normal tissue by a substantial increase in the formation and secretion of proteases. The active agents can be targeted by technique of the instant invention to many different diseases including but not limited to tumors like renal cell carcinoma, prostate cancer, breast cancer, pancreatic cancer and melanoma. The strategy can be used for treatment of inflammatory diseases and can target the delivery to disease sites such as multiple sclerosis, autoimmune arthritis, and some other immune diseases. Treatment of other diseases would benefit from a targeted delivery of biologically active molecules as well. The therapeutic strategy of the instant invention can be used as a stand-alone or as adjuvant to other treatments such as chemotherapy, or radiation therapy for cancer or hormonal therapy for immune diseases. The treatment could be used for advanced disease like metastatic cancers as well as for newly diagnosed disease, residual disease, recurrent disease, as prophylactic therapy, or for potentially cured disease like completely resected tumors. The inhibitor can be administered alone or together with biologically active agent and can be delivered as biologics intravenously, intraepidermally, or intramuscularly or can be administered in a biodegradable polymer, or as a gene or cell therapy.

DETAILED DESCRIPTION OF THE PREFERRED EMBODIMENTS

Chimeric inhibitor, inhibitor, first moiety: The inhibitor is a peptide, a cyclic peptide, a polypeptide, a peptidomimetic, a protein, a fusion protein, a hybrid molecule or a dimer, multimer, or a conjugate of the above that binds, inhibits, suppresses, neutralizes, or decreases activity of a biologically active agent and contains a peptide, a polypeptide, a lipid, a carbohydrate, a polysaccharide, a glycolipid, a nucleic acid, or a conjugate of the above susceptible to cleavage by a specific reagent produced by a target cell or other cleaving reagent. The inhibitor is also an oligonucleotide sequences encoding a polypeptide that binds, inhibits or neutralizes a ligand or active agent and contains an oligonucleotide sequences encoding a peptide susceptible to cleavage by a specific protease or other peptide cleaving reagent. The inhibition can be binding, inhibition, inactivation, neutralization, suppression, or decrease of activity of an active agent and can be caused by binding, association, any interaction, or by inhibition of the agent activator. Preferred inhibitors of the present invention include a naturally occurring inhibitor, a receptor, a soluble receptor, an antibody, a polyclonal antibody, a monoclonal antibody, a bispecific antibody, an antibody fragment, a single chain antibody, anti-idiotype antibodies, a peptabody, a peptide, an oligopeptides, an oligonucleotide, a cyclic peptide (ie. a peptide that is circular in nature), a peptide-lipid conjugate, a hormone, an antigen, an epitope, a receptor, a chemokine, a nucleic acid, a ligand or a dimer, multimer, or a conjugate of the above. Naturally occurring inhibitors are inhibitors that inhibit active agents and are found in nature, examples include TIMP, alpha 1-antichymotrypsin, alpha 2-macroglobulin and the like. Hybrid molecule is a molecule comprising of at least two parts of different nature for example peptide-chemical drug, peptide-lipid, carbohydrate-nucleic acid and the like. Preferred inhibitor is an antibody inhibitor, a monoclonal antibody inhibitor, a bispecific antibody inhibitor, a catalytic antibody inhibitor, a peptabody inhibitor, a receptor inhibitor, an Fc receptor inhibitor, a hormone inhibitor, a peptide inhibitor, a cyclic peptide inhibitor, a peptide-lipid conjugate inhibitor, a peptide-nucleic acid conjugate inhibitor, a nucleic acid/protein conjugate inhibitor, a delivery-enhancing transporter inhibitor, a pepducin inhibitor, a cytokine inhibitor, a chemokine inhibitor, a circularly permuted chemokine inhibitor, an interleukin inhibitor, an interferon inhibitor, or a dimer or multimer of the above and the like. Another preferred inhibitor moieties of the present invention include an antiviral protein, a cytokine receptor, the moiety of a cytokine receptor which is external to the cell, a cytokine antagonist, a growth factor, a growth factor receptor, the moiety of a growth factor receptor which is external to the cell, and the like. Inhibitor-ligand pair: A set of molecules that demonstrate specific binding, generally of relatively high affinity. Exemplary inhibitor ligand pairs include ligand/antibody, ligand/antibody fragment, ligand/single-chain antibody, hapten/antibody, zinc finger protein/DNA fragment, enzyme/inhibitor, lectin/carbohydrate, peptide/receptor, peptide/peptide, and ligand/receptor. Lower molecular weight forms of the ligand or anti-ligand molecules that bind with complementary anti-ligands or ligands are also contemplated by the present invention. Biologically active agent, active agent, (biologically) active compound, biological response modifier, or ligand (can be used interchangeably): Are molecules that regulate the immune response to disease cells including stimulation of cells to secrete immune-augmenting cytokines, chemokines, a inhibitory peptide, molecules like interleukines (IL), IL-1, IL-2, GM-CSF, IFN, and IL 12, colony stimulating factor (CSF), GM-CSF, interleukins, interferons, colony stimulating factors, a coagulation factor, a fibrinolytic protein, a photosensitizing agent, or an imaging agent, a biological activation cascade or a component of this cascade, a component of the coagulation system, a component of fibrinolysis system, a component of the complement system, the kinin system, an enzyme which converts the inactive precursor of a pharmacological substance into the pharmacologically active substance, antibodies, peptides, muteins of the above, a pharmacologically active substance, macromolecular drugs, chemical drugs, and the like are contemplated. Targeted delivery: Is characterized by an improved targeting ratio or increased absolute dose to the target sites in comparison to conventional therapy. The present invention provides for effective delivery of active agents such as antibodies, chemokines, cytokins, toxins, peptides and photosensitizing agents by using the inhibitor of present invention. The non-target tissues are less affected by effects of the active agent. Targeting: Involves target site localization of a targeting moiety that is conjugated with one member of an inhibitor-ligand pair. Targeting moiety, a recognition domain (can be used interchangeably): A molecule that binds to a defined population of cells. The targeting moiety may bind a receptor, an oligonucleotide, an enzymatic substrate, an antigenic determinant, or other binding site present on or in the target cell population. Antibody is used throughout the specification as a prototypical example of a targeting moiety. Antibody fragments and small peptide sequences capable of recognizing expressed antigen are also contemplated targeting moieties within the present invention. Tumor is used as a prototypical example of a target in describing the present invention. Association of targeting moiety with the inhibitor or active agent can be covalent, non-covalent or other genus. Target cell: A cell that express a specific reagent produced by a target cell, for example a protease or other peptide cleaving reagent that is capable to cleave a specific cleavage site, a peptide or a second moiety. Target cells such as tumor cells, leukemia cells, endothelial cells, macrophages, lymphocytes, muscle cells, epithelial cells, glia cells, synovial cells, rheumatoid arthritis cells or virus-infected cells and the like are contemplated. Product of target cells, a specific reagent produced by a target cell, an enzyme, a protease, a reagent (can be used interchangeably): The reagent can be secreted, membrane bound, or intercellular. The reagent can be a protease, a lipase, a nuclease, or a glycolytic enzyme that cleaves sugars, carbohydrates and the like. A protease can be a prostate specific antigen, plasminogen activator, cathepsin, matrix metalloproteinase, viral protease, HIV protease, a catalytic antibody, catalytic RNA, a peptidase (enzyme capable of cleavage of the peptidyl linker) or other peptide cleaving reagent and the like are contemplated. Cleavage site, peptide, polypeptide specifically cleavable, second moiety: A polypeptide, a lipid, a carbohydrate, a polysaccharide, a glycolipid, a nucleic acid, or a conjugate of the above susceptible to cleavage by a reagent and the like are contemplated. A peptide comprising usually of 3 to 100 amino acids which can be specifically cleaved by a protease or other peptide cleaving agent. Operably linked means any link that makes the inhibitor functional can be covalent or non-covalent in nature. Treating is improving or worsening a condition of a cell or tissue. Conjugate: Encompasses fusion proteins, chemical molecule/peptide conjugates, chemical conjugates, covalently or non-covalently bound molecules, and the like. Fusion protein is a protein not found in nature. Associates with: Association that can be covalent, noncovalent or other genus. Fusion protein, hybrid protein, chimera: A protein which is not found in nature. Dimer: Two peptides, polypeptides or molecule of any nature either joined by a covalent bond or associated by a noncovalent interaction. A dimer can be a homodimer, or heterodimer. The subunits can be linked by a linker, joined directly or associated a by noncovalent interaction. Multimer: more than two unit (first or second moiety) molecule. Adjuvant: An ingredient that improves the action of an administered compound. Vector: A polynucleotide used for DNA manipulation, amplification and/or expression of polypeptides. Examples of a vector include a plasmid, virus, viral vector, RNA, or DNA fragment. Animal, vertebrate, mammal, human (can be used interchangeably): Any vertebrate. The term vertebrate as used herein includes all members of the animal kingdom including mammals, preferably humans.

In preferred embodiment of this invention, the inhibitor is constructed by inserting one or more peptides, which can be cleaved specifically by an enzyme (or other peptide cleaving agent) produced by vertebrate cells, into or next to an inhibitor. The inhibitor of instant invention binds and inactivates or decreases activity of an active agent. Binding of the inhibitor to an active agent causes activity reduction of said agent, cleavage of the inhibitor causes restoration of activity of said active agent. Restoration means bringing the activity closer to its original state. Cleavage of the inhibitor by a reagent makes the inhibitor deactivatable by said reagent; the inhibitor decreases its binding, inhibiting, suppressing, activating, or neutralizing activity for an active agent. Decrease of the activity can be anywhere from 5% to 100%, preferably in excess of 70%, most preferably in excess of 80%, and even more preferably in excess of 90%, 95% or 99%. When the inhibitor is cleaved by an enzyme the interaction between the inhibitor and an active agent is compromised and the active agent is released and rendered active. The activity means any function the active agent has in its free form, for example binding activity, inhibiting activity, suppressing activity, toxicity, therapeutic activity, stimulating activity, activating activity, or neutralizing activity. The activity of an active agent can be restored, activated, or rendered active, to anywhere from 5% to 100% of its original activity, preferably in excess of 70%, most preferably in excess of 80%, and even more preferably in excess of 90%, 95% or 99%. Moiety specifically cleavable by a reagent produced by a target cell means that the reagent has a cleavage specificity for the moiety anywhere from 5% to 100%, preferably in excess of 70%, most preferably in excess of 80%, and even more preferably in excess of 90%, 95% or 99%. In preferred embodiment of this invention, a method of site specific activation of an active agent is accomplished by administration of the inhibitor alone or together with active agent. In a target site, a reagent produced by target cells inactivates the inhibitor causing activation of the active agent specifically in the target site. Specific cleavage of a second moiety causes reduction of binding, inhibiting, suppressing, or neutralizing activity of the inhibitor and restoration of activity of an active agent. Said inhibitor can be administered alone or together with an active agent such that the activity or toxicity of the active agent is reduced until it reaches a target cell producing a reagent wherein the inhibitor is cleaved by a reagent and activity of said active agent is restored. Second moiety embedded within the first moiety means that the second moiety is inserted anywhere into the first moiety. First and second moieties connected by a linker means that there is a linker between the first and second moieties and the connection can be covalent or non-covalent. The linker can be of any chemical or biological nature.

In preferred embodiment of this invention, the active agent (active compound) can be a cytostatic, cytotoxic or inflammation-eliciting protein, such as perforin, granzyme, cytokines, such as IL-1, IL-2, TL-4, IL-12, IL-3, IL-5, human leukemia inhibitory factor (LIF), IL-7, IL-11, IL-13, GM-CSF, G CSFb or M-CSF, interferons, such as IFN.alpha., IFNβ or IFN.gamma., TNF, such as TNF.alpha. or TNFβ, oncostatin M, sphingomyelinase, magainin and magainin derivatives or chemokines, such as RANTES (MCP-2), monocyte chemotactic and activating factor (MCAF), IL-8, macrophage inflammatory protein 1 (MIP-1.alpha. or MIP-1β) or neutrophil activating protein 2 (NAP-2). The active compound can also be an antiangiogenic protein, such as angiostatin, interferons, such as IFN.alpha., IFNβ or IFN.gamma., platelet factor 4, IL-12, TIMP-1, TIMP-2 or TIMP-3. The active compound can also be an enzyme which is able to convert an inactive precursor of a pharmacological active substance, for example a cytostatic agent, into the active substance itself. Examples of such active compounds are bacterial nitroreductase, bacterial β-glucuronidase, plant β-glucuronidase derived from *Secale cereale*, human β-glucuronidase, human carboxypeptidase (CB), e.g. mast cell CB-A or pancreas CB-B, or bacterial carboxypeptidase, bacterial β-lactamase, bacterial cytosine deaminase, human catalase or peroxidase, phosphatase, in particular human alkaline phosphatase or human acid prostate phosphatase, type 5 acid phosphatase, oxidase, in particular human lysyl oxidase or human acid D-aminooxidase, peroxidase, in particular human glutathione peroxidase, human eosinophilic peroxidase or human thyroid peroxidase. The active compound can also be a protein which affects the immune system, for example a protein having an antiallergic effect, such as IFNβ, IFN.gamma., IL-10, soluble IL-4 receptors, IL-12 or TGFβ, or a protein which can prevent the rejection of transplanted organs, such as IL-10, TGFβ, soluble IL-1 receptors, soluble IL-2 receptors, IL-2 receptor antagonists or soluble IL-6 receptors, or a protein for the therapy of antibody-mediated autoimmune diseases, for example TGFβ, IFNβ, IFN.gamma., IL-12, soluble IL-4 receptors or soluble IL-6 receptors, or a protein for the therapy of cell-mediated autoimmune diseases, for example IL-6, IL-9, IL-10, IL-13, TNF.alpha., IL-4 or TNFβ, or a protein for the therapy of arthritis. According to the present invention, structural genes can also be selected whose expressed protein directly or indirectly inhibits inflammation, for example in a joint, and/or promotes the reconstitution of extracellular matrix (cartilage and connective tissue) in the joint. These expressed proteins include, for example, IL-1 receptor antagonists (IL-1-RA), since IL-1-RA inhibits the binding of IL-1.alpha. and IL-1β, soluble IL-1 receptor, since soluble IL-1 receptor binds and inactivates IL-1, IL-6, since IL-6 increases secretion of TIMP and superoxides and decreases secretion of IL-1 and TNF.alpha. by synovial cells and chondrocytes, soluble TNF receptor, since soluble TNF receptor binds and activates TNF, IL-4, since IL-4 inhibits the formation and secretion of IL-1, TNF.alpha. and MMP, IL-10, since IL-10 inhibits the formation and secretion of TNF.alpha. and MMP and increases the secretion of TIMP, insulin-like growth factor (IGF-1), since IGF-1 stimulates the synthesis of extracellular matrix, TGFβ, especially TGF and TGF, since TGFβ stimulates the synthesis of extracellular matrix superoxide dismutase, or TIMP (tissue inhibitors of metalloproteinases), especially TIMP-1, TIMP-2 or TIMP-3. The active compound can also be a protein for relieving damage to the nervous system, for example a growth factor, such as FGF, nerve growth factor (NGF), brain-derived neurotrophic factor (BDNF), neurotrophin 3 (NT-3), neurotrophin 4 (NT-4) or ciliary neurotrophic factor (CNTF), or a cytokine, or a cytokine inhibitor, which is able to inhibit or neutralize the neurotoxic effect of TNF.alpha., for example TGFβ, soluble TNF receptors, IL-10, since IL-10 inhibits the formation of IFN.gamma., TNF.alpha., IL-2 and IL-4, soluble IL1 receptors, such as IL-1 receptor I or IL-1 receptor II, since soluble IL-1 receptors neutralize the activity of IL-1, IL-1 receptor antagonist or soluble IL-6 receptors and the like. The active compound can also be a protein which stimulates angiogenesis, for example VEGF or FGF. The active compound can furthermore be a protein which lowers blood pressure, for example kallikrein or endothelial cell nitric oxide synthase. The active compound can also be a protein for the therapy of chronic infectious diseases, for example a protein which exhibits cytostatic or cytotoxic effects, or an enzyme which cleaves a precursor of an antiviral or cytotoxic substance into the active substance, or a cytotoxin having an antiviral effect or a growth factor having an antiviral effect. Examples are IFN.alpha., IFNβ, IFN.gamma., TNFβ, TNF.alpha., IL-1 or TGFβ.

In preferred embodiment of this invention, the inhibitor is constructed from one or more receptor molecule, soluble receptor, antibody, antibody fragment, single chain antibody, their pegylated forms and the like. Examples of receptors include but are not limited to a cytokine receptor, a growth factor receptor; a Fc receptor, a receptor or of a viral glycoprotein, or a glycophospholipid anchor, TRAIL receptor, VEGF receptor, hormone receptor, IL-1 receptor, IL-1 alpha receptor, IL-1 beta receptor, IL-2 receptor, IL-3 receptor (alpha subunit), IL-3 receptor (beta subunit), IL-4 receptor, IL-6 receptor, IFN gamma receptor, IL-7 receptor, IL-8 receptor, IL-9 receptor, IL-10 receptor, IL-11 receptor, GM-CSF receptor, IL-12 receptor, IL-13 receptor, LIF receptor, macrophage colony stimulating factor (M-CSF) receptor, granulocyte macrophage colony stimulating factor (GM-CSF) receptor, lymphotoxin alpha receptor, the moiety of a cytokine receptor which is external to the cell, a receptor-binding part sequence of these ligands the extracellular moiety of an Fc receptor, type I and II macrophage scavenger receptors, MAC-1 (leukocyte function antigen) receptor, LFA-1 alpha (leukocyte function antigen) receptor or p150,95 (leukocyte function antigen) receptor, muteins of the above and the like. A receptor-immunoglobulin G (IgG) fusion proteins can be constructed and used as the chimeric inhibitors. They have longer half-lives in vivo in comparison with soluble receptors, consisting of the extracellular region of the native sequence. For example, a fusion protein comprising the extracellular domain of a receptor, a polypeptide cleavable by an enzyme, and the hinge, CH2 and CH3 domains of the human IgG constant region can be constructed. The constant region can also be fused to two receptors. For example, GM-CSF alfa and GM-CSF beta receptors are fused with IgG Fc U.S. Pat. No. 5,447,851. DNA encoding a chimeric polypeptide comprising the extracellular domain of TNF receptor can be fused to IgG.

In preferred embodiment of this invention, the inhibitor can be a dimer and constructed from two or more molecules like drugs, proteins, peptides and the like either linked by a linker like polyglycine serine linker, chemical linker, joint directly, or joint by a noncovalent association like using a fusion with a portion of IgG molecule and the like. A drug, chemical drug or, macromolecular drug are any pharmaceutical entities used for treatment of a condition in a vertebrate preferably human. Dimers can be constructed by adding a cysteine residue to the C-terminus of inhibitor peptides and crosslinking them with a chemical linker like homobifunctional reagent [Park, 2000]. Cysteine-containing peptides can be mixed with 1,6-hexane-bis-vinylsulfone in 0.1 M sodium borate buffer (pH 8.5) and incubated at 25° C. for 3 hours before stopping the reaction with cysteine. Use of an optimized or conformational constraint crosslinker could increase dimer affinity even further. Peptide inhibitors can be crosslinked with varying length alkyl-chains containing either a single double bond, or a triple bond to remove degrees of freedom within the tethers. Crosslinked dimers can be purified by HPLC and verified by mass spectrometry and amino acid sequencing. The chimeric dimer structure can be as follows: A peptide—P site—C --- C—editpep A. In general, dimers have higher affinity for their ligands than monomers. For example, an inhibitor that has a cleavage site inserted between the dimer subunits, or in the linker can be constructed. Multimers are also contemplated in one embodiment, for example a new type of high avidity binding molecule can be created by harnessing the effect of multivalent interaction and is contemplated. A short peptide inhibitor can be fused via a semirigid hinge region with the coiled-coil assembly domain of the cartilage oligomeric matrix protein, resulting in a pentameric multivalent binding molecule. Dextran and similar molecules can also serve as a backbone for multimers. Molecules preferably with 3 to 100 multivalent binding sites are contemplated. Dimers and multimers can be constructed from same, similar or different first moieties. Dimers and multimers can also contain more that one site (second moiety) specifically cleavable by a reagent produced by a cell, for example a peptide specifically cleavable by a protease. These second moieties can be same in nature and structure, similar or different. These sites can be cleavable by same or different reagents, for example a protease and a nuclease. Typically, covalent attachment can be accomplished by construction of fusion peptides or proteins or by the use of chemical linkers. Dimers and multimers can contain same, similar or different linkers, for example a peptide linker and an alkyl-chain chemical linker. Dimers and multimers can contain cyclic peptides. Peptides flanked by cysteine residues on each side can make the peptides cyclic. This approach emphasizes the importance of conformational restriction as a means of improving the potency of peptide binding. Such a way of designing effective peptides restricts the peptide conformation with a cyclizing bond. Restraining conformational freedom of a peptide could favor selection of high affinity binders.

In preferred embodiment of this invention, the inhibitor can be constructed from a ligand, cytokine, chemokine, biological response modifier, and the like. For example, a GM-CSF molecule that forms dimers binding a second GM-CSF molecule. In preferred embodiment of this invention, the inhibitor can be constructed from a peptidomimetics. A peptidomimetic is a molecule of any chemical nature that mimics a peptide, protein, antigen and the like. For example, an exocyclic small peptidomimetics corresponding to critical binding sites of a cytokine or an antibody. In preferred embodiment of this invention, the inhibitor is a chimera between one or more antibody, antibody fragment, or single chain antibody and one or more receptor and the like and contains one or more peptides specifically cleavable by a protease or other peptide cleaving agent. In preferred embodiment of instant invention, the inhibitor is an neutralizing antibody, which has at least 20% neutralizing activity against an active agent. In preferred embodiment of instant invention, the inhibitor is an anti-idiotype antibody, for example, antibody directed against catalytic antibody. In preferred embodiment of instant invention, the inhibitor is a catalytic antibody, which has at least 20% activity for its substrate.

In preferred embodiment of this invention, the inhibitor inhibits binding of an antibody to its antigen. The inhibitor is an antigen or antigen-like molecule and contains one or more peptides or oligopeptides which can be cleaved specifically by an enzyme produced by vertebrate cells. Ideally, the binding affinity of the the antibody for the inhibitor (when a peptide containing the enzyme cleavage site is incorporated into the inhibitor and is intact) is similar, slightly reduced or increased compared to the unmodified antigen. Also ideally, the neutralizing or inhibiting activity of the inhibitor is greatly reduced or absent upon proteolytic cleavage of the peptide encoding the cleavage site releasing active antibody into the environment. For example, the specificity of monoclonal antibodies for HER-2/neu expressed on tumor tissues is increased by the inhibitor of the instant invention; the specificity of monoclonal antibodies for EGFR expressed on tumor tissues is increased by the inhibitor of the instant invention.

In preferred embodiment of this invention, the inhibitor inhibits binding of a homing peptide to its target tissue. This inhibition is compromised upon a cleavage of the inhibitor by an enzyme produced by vertebrate cells. Certain peptides home to specific sites in specific tissues, tumor homing peptides target tumor vasculature having a surprising degree of specificity in the endothelia tissues. For example, a peptide SMSIARL (SEQ.ID.NO.: 1) homes to prostate tumor vasculature. Peptides for homing to the prostate vasculature reveal tissue-specific features in the blood vessels of the prostate. Tumor-homing peptides have been used to direct therapies into tumors. Peptides that home to the vasculature of the prostate are used to deliver therapeutic agents, for example a proapoptotic peptide, to the prostate. A peptide capable of homing to the blood vessels in the prostate can target a proapoptotic peptide to the prostate, and that systemic treatment with this targeted compound can cause destruction of prostate tissue and delay the development of prostate cancer. Alternatively, the homing peptide can be part of the inhibitor as a targeting moiety.

In preferred embodiment of this invention, the inhibitor inhibits a transporter peptide that promotes transport of an agent across the biological membrane at a rate that is greater than the trans-membrane transport rate of the biological agent in non-conjugated or free form. This inhibition is compromised upon inhibitor cleavage by an enzyme produced by vertebrate cells. The transporter peptide is a polymer that consists of from 6 to 25 subunits, at least 50% of which contain a guanidino or amidino sidechain moiety, wherein the polymer contains at least 6 guanidino or amidino sidechain moieties. Preferably, no guanidino or amidino sidechain moiety is separated from another such moiety by more than one non-guanidino or non-amidino subunit. In a more specific embodiment, the polymer contains at least 6 contiguous subunits each containing either a guanidino or amidino group, and preferably at least 6 or 7 contiguous guanidino sidechain moieties (U.S. Pat. No. 6,306,993).

In preferred embodiment of this invention, the inhibitor inhibits biologic response modifiers. This class is defined by the ability to target specific cellular events involved in the pathogenesis. For example, agents for neutralizing TNF. In preferred embodiment of this invention, the inhibitor can cause production of matrix metalloelastase elastase that causes production of angiostatin or endostatin, which inhibits angiogenesis and suppress the growth of tumors and metastases. In preferred embodiment of this invention, the inhibitor is used for targeted delivery of ligands (active agents) to a site of a disease including but not limited to a tumor. For example, administration of cytokines or therapeutic agents is accompanied by some disadvantages like systemic toxicity. The goal of targeted delivery is to achieve an optimal concentration of an active agent to maximize exposure of target tissue, while remaining the levels in non-target tissues below the threshold of unacceptable organ toxicity and exposure. The inhibitor of the instant invention may bind and neutralize a ligand decreasing or eliminating ligand's toxicity. When the inhibitor is cleaved thus deactivated by an enzyme released for instance by a tumor cells the ligand is rendered active hence delivered specifically to tumor site. Anti-tumor agents, such as IL-2, TNF, GM-CSF, IFN-gamma, or multiple drug resistance protein may be employed as ligands inhibited by the inhibitor and delivered in a targeted manner to tumor sites in the practice of protocols of the present invention.

Functional equivalents of the aforementioned molecules are also useful as inhibitor moieties of the present invention. One inhibitor moiety functional equivalent is a "mimetic" compound, an organic chemical construct designed to mimic the proper configuration and/or orientation for inhibitor/ligand binding. Another inhibitor functional equivalent is a short polypeptide designated as a "minimal" polypeptide, constructed using computer-assisted molecular modeling and mutants having altered binding affinity, which minimal polypeptides exhibit the binding affinity of the inhibitor. In preferred embodiment of this invention, the oligopeptide that is selected for incorporation into a polypeptide encoding an inhibitor will be chosen both for its selective, enzymatic cleavage by an enzyme and for the ability not to interfere significantly with the binding, neutralizing or inhibiting activity of the inhibitor-oligopeptides chimera (or, in what is felt to be an ideal situation, the modified inhibitor) which results from such an incorporation.

In preferred embodiment of this invention, the inhibitor contains one or more peptides, or second moieties or oligopeptides which can be cleaved specifically by an enzyme or cleaving agent produced by vertebrate cells. Ideally, the binding, neutralizing, inhibiting, suppressing, or decreasing activity of a biologically active agent of the inhibitor is the same as for unmodified inhibitor (such as, but not limiting to a peptide, a soluble receptor or antibody), slightly reduced or increased when the polypeptide containing the enzyme cleavage site is incorporated into the inhibitor and is intact. Also ideally, the neutralizing or inhibiting activity of the inhibitor is greatly reduced or absent upon proteolytic cleavage of the cleavage site. Also ideally, the activity of the ligand, active agent, increases significantly or returns to the activity of the unbound ligand upon proteolytic cleavage of the inhibitor. While it is not necessary for practicing this aspect of the invention, the most preferred embodiment of this aspect of the invention is an inhibitor-oligopeptide chimera wherein the oligopeptide in the inhibitor is cleaved by the proteolytic activity of a protease or any other native proteolytic enzymes present in the tissue proximity, thereby releasing the active compound, which was bound by the inhibitor, into the physiological environment at the place of proteolytic cleavage. It is understood that the oligopeptide or peptide of the instant invention that is conjugated to the inhibitor does not need to be the oligopeptide that has the greatest recognition and is most readily proteolytically cleaved by an enzyme, for example, a protease, catalytic antibody, or catalytic RNA. Thus, the oligopeptide or second moiety that is selected for incorporation in such an inhibitor will be chosen both for its selective cleavage and for the ability not to interfere with the activity of the inhibitor-polypeptide conjugate (or, in what is felt to be an ideal situation) which results from such a cleavage. The inhibitor of the instant invention may contain more than one polypeptide containing the cleavage site and further comprise additional sequences that may compensate for undesired consequences of inserting a polypeptide containing the cleavage site into the inhibitor. Inhibitors of the invention can be used for modifying a given biological response, the inhibitor is not to be construed as limited to inhibitors found in vertebrate cells, antibody, antibody fragment, classical chemical inhibitors, receptors, soluble receptors, fragments of receptors etc. For example, the inhibitor may be a protein or polypeptide possessing a desired biological activity. In one embodiment, said oligopeptides which are specifically recognized by a reagent released from vertebrate cells and are capable of being cleaved by the enzymatic activity. Such oligopeptides include oligomers that comprise of 3 to 100 amino acids. For example, the active agent may be a protein or polypeptide possessing a desired biological activity. For example, such proteins may include tumor necrosis factor (TNF), alpha-interferon, beta-interferon (IFN), lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor, platelet derived growth factor, tissue plasminogen activator, or other growth factors, biological response modifiers, or a toxin such as abrin, ricin A, *pseudomonas* exotoxin, or diphtheria toxin and the like. One skilled in the art may make modifications to the inhibitor or ligand agents in order to make reactions of the agents more convenient for purposes of the invention.

Throughout this specification, any reference to an inhibitor should be construed to refer to each of the inhibitors identified and contemplated herein and to each biologically equivalent molecule and substantially homologous molecule. By "biologically equivalent" as used throughout the specification and claims, we mean compositions of the present invention which are capable of preventing action of an active agent in a similar fashion, but not necessarily to the same degree. By "substantially homologous" as used throughout the ensuing specification and claims, is meant a degree of homology to an inhibitor in excess of that displayed by any previously reported inhibitor. Preferably, the degree of homology is in excess of 70%, most preferably in excess of 80%, and even more preferably in excess of 90%, 95% or 99%. A particularly preferred group of inhibitors are in excess of 95% homologous with the native inhibitor. The percentage of homology as described herein is calculated as the percentage of amino acid residues found in the smaller of the two sequences which align with identical amino acid residues in the sequence being compared when four gaps in a length of 100 amino acids may be introduced to assist in that alignment.

In preferred embodiment of the invention, the inhibitor cleavage by said reagent causes reduction of inhibitory activity of said inhibitor. In preferred embodiment of the invention, target cells cause reduction of inhibitory activity of said inhibitor by production of a reagent which cleaves said inhibitor. In preferred embodiment of the invention, a composition that comprises the inhibitor reduces the activity or toxicity of an active agent by contacting or binding the active agent such that the activity or toxicity of the agent is reduced. Preferred embodiment of the invention is a method of reducing the activity or toxicity of a active agent comprising contacting the active agent with the inhibitor such that the activity or toxicity of the agent is reduced. In preferred embodiment of the invention, administration of a biologically effective amount of a composition that comprises the inhibitor alone or together with an active agent to a vertebrate such that the activity or toxicity of the active agent is reduced until it reaches a target cell that produces a reagent wherein the inhibitor is cleaved by said reagent such as inhibitory activity of said inhibitor is reduced and activity of said active agent is restored. In preferred embodiment of the invention, the inhibitor is administered alone, co-administered with an active agent, or co administered with an active agent and an adjuvant, a pharmaceutically acceptable carrier, a diluent, or an excipient to a vertebrate. In preferred embodiment of the invention, the administration to a vertebrate is only one of several different treatments. In preferred embodiment of the invention, administration of a biologically effective amount of a composition that comprises the inhibitor alone or together with an active agent to a vertebrate inhibits growth of a cancer.

In preferred embodiment of the invention, said enzyme is a protease, examples of these proteases include but are not limited to prostate specific antigen (PSA); matrix metalloproteinases (MMP), such as collagenases, for example of groups I, II, III, IV or V; stromelysin 1, stromelysin 2 or stromelysin 3; metrilysins; plasminogen activator of the urokinase type or tissue plasminogen activator; gelatinases, such as gelatinase A (MMP 2), and progelatinase B (MMP 9) and progelatinase A; cathepsins, such as cathepsin B, cathepsin D, cathepsin L, cathepsin E or cathepsin H, or their precursors (procathepsins); tumor cell surface proteases; elastase; pancreatic trypsinogens; virus encoded proteases, HIV protease, hepatitis protease, muteins of the above and the like. Angiogenesis, inflammation, and cancer invasion are linked to the overexpression of matrix metalloproteinases (MMPs), which destroy the extracellular matrix. MMPs belong to the group of endogenous proteases which are able to degrade various components of extracellular matrix, such as collagen, elastin and gelatin. Levels of various MMPs are elevated in cancerous tissue. A positive correlation between MMP expression and increased invasiveness and progression has been demonstrated in a wide range of human cancers (breast, colon, lung and prostate). MMP-2 can be localized in a proteolytically active form on the surface of invasive cancer cells and facilitate cell-mediated collagen degradation. Expression of MMP-9 is restricted, and in normal quiescent tissues is typically low or absent. However, MMP-9 expression is induced under conditions that require tissue remodeling including tumor invasion. Cysteine proteases, aspartic proteases and serine proteases are also found specifically in tumor cells. MMPs 2, 9, 13, and MMP-15 were found to be exclusively expressed in rheumatoid arthritis that had degenerative matrix changes. Association between increased MMP-9 levels and inflammatory arthritis has been well documented. The tumor-associated serine protease plasmin, its activator uPA (uro-kinase-type plasminogen activator), the receptor uPA-R (CD87), and the inhibitors PAI-1 and PAI-2 are linked to cancer invasion and metastasis. In cancer, increase of uPA, uPA-R, and/or PAI-1 is associated with tumor progression and with shortened disease-free and/or overall survival in patients afflicted with malignant solid tumors. Matriptase is an epithelial-derived, integral membrane serine protease. The enzyme was initially isolated from human breast cancer cells and has been implicated in breast cancer invasion and metastasis. Peptidases secreted by diseased cells that recognize various peptides, for example peptidases cleaving substrate N-succinyl-alanyl-leucyl-alanyl-leucyl are also contemplated.

In one embodiment of the invention, said protease is a prostate specific antigen (PSA) that is a single chain 33 kDa glycoprotein produced almost exclusively by the human prostate epithelium. PSA is a protease with chymotrypsin-like specificity, which is responsible for dissolution of the gel structure formed at ejaculation by proteolysis of the major proteins in the sperm entrapping gel, Semenogelin I and Semenogelin II, and fibronectin generating several soluble Semenogelin I and Semenogelin II fragments and soluble fibronectin fragments with liquefaction of the ejaculate and release of progressively motile spermatozoa. PSA may proteolytically degrade IGFBP-3 (insulin-like growth factor binding protein 3) allowing IGF to stimulate specifically the growth of PSA secreting cells. PSA complexed to alpha 1-antichymotrypsin is the predominant molecular form of serum PSA and may account for up to 95% of the detected serum PSA. The prostatic tissue (normal, benign hyperplastic, or malignant tissue) is implicated to predominantly release the mature, enzymatically active form of PSA, as this form is required for complex formation with alpha 1-antichymotrypsin. Therefore, in the microenvironment of prostatic PSA secreting cells the PSA is believed to be processed and secreted in its mature enzymatically active form not complexed to any inhibitory molecule. PSA also forms stable complexes with alpha 2-macroglobulin, but as this results in encapsulation of PSA and complete loss of the PSA epitopes. A free, noncomplexed form of PSA constitutes a minor fraction of the serum PSA. Free serum PSA doesn't have enzymatic activity. Prostate metastases are known to secrete enzymatically active PSA. PSA has also been suggested to regulate invasiveness and metastatic potential of prostatic tumors. The prostatic tissue (normal, benign hyperplastic or malignant) releases the mature enzymatically active form of PSA not complexed to any inhibitory molecule. Once PSA reaches the blood, it is complexed to its natural inhibitor, 1 antichymotrypsin, and becomes enzymatically inactive. Prostate cancers and cancer metastases obtained directly from patients secrete large amounts of active PSA. Therefore, a compound that could be deactivated by the proteolytic activity of PSA should be prostate cell specific as well as specific for PSA secreting prostate metastases. On the basis of this information, it is possible to use the PSA substrate peptides to target peptide-containing inhibitors in complexes with active compounds for selective deactivation within sites of PSA-secreting, metastatic prostate cancer cells and not within the blood or other nonprostatic normal tissues. The proteases mentioned above and other peptide cleaving agents are contemplated in the instant invention U.S. Pat. Nos. 5,599,686 and 6,410,514.

In another embodiment, the second moiety is a peptide, which comprises a sequence cleavable by a protease.

In another embodiment, the second moiety or the cleavage recognition site comprises an amino acid sequence with 70% or greater sequence homology to amino acids SKGSFSIQYTYHV (SEQ ID NO:2), HLGGSQQLLHNKQ (SEQ ID NO:3), SKGKGTSSQYSNTE (SEQ ID NO:4), DRVYIHPF (SEQ ID NO:5), VVCGERGFFYTP (SEQ ID NO:6), FFYTPKA (SEQ ID NO:7), KRRPVKVYP (SEQ ID NO:8), PVGKKRRPVKVY (SEQ ID NO:9), KPVGKKRRPVKV (SEQ ID NO:10), GKPVGKKRRPVK (SEQ ID NO:11), TFAGNAVRRSVGQ (SEQ ID NO:12), PLGLWA (SEQ ID NO:13), PLFYS (SEQ ID NO:14), PRTLT (SEQ ID NO:15), or PLRLS (SEQ ID NO:16), HSSKLQ (SEQ ID NO:17), SQYSNT (SEQ ID NO:18), QFYSSNK (SEQ ID NO:19), VSQNYPIVQNFN (SEQ ID NO:20); SKARVLAEAMSN (SEQ. ID. NO:21), SIRKILFLDGIN (SEQ ID NO:22), SAPQVLPVMHPN (SEQ ID NO:23), SKTKVLWQPKN (SEQ ID NO:24), SKTKVLVVQPRN (SEQ ID NO:25), STTQCFPILHPN (SEQ ID NO:26); SGVVNASCRLAN (SEQ ID NO:27), SSYVKASVSPEN (SEQ ID NO:28), SALVNASSAHVN (SEQ ID NO:29), STYLQASEKFKN (SEQ ID NO:30), SSILNASVPNFN (SEQ ID NO:31), SQDVNAVEASSN (SEQ ID NO:32), SVYLQASTGYGN (SEQ ID NO:33), SKYLQANEVITN (SEQ ID NO:34), SELRTQSFSNWN (SEQ ID NO:35), SELWSQGIDDDN (SEQ ID NO:36), DLEVVTSTWVFN (SEQ ID NO:37), DEMEECASHLFN (SEQ ID NO:38), EDVVCCSMSYFN (SEQ ID NO:39), KGWRLLAPITAY (SEQ ID NO:40), SKPAKFFRLNFN (SEQ ID NO:41), SKPIEFFRLNFN (SEQ ID NO:42), SKPAEFFALNFN (SEQ ID NO:43), SLLKSRMVPNFN (SEQ ID NO:44), SLLIARRMPNFN (SEQ ID NO:45), SKLVQASASGVN (SEQ ID NO:46), SSYLKASDAPDN (SEQ ID NO:47), RPKPQQFFGLMN (SEQ ID NO:48), SLRPLALWRSFN (SEQ ID NO:49), SPQGIAGQRNFN (SEQ ID NO:50), DVDERDVRG-FASFL (SEQ ID NO:51), SLPLGLWAPNFN (SEQ ID NO:52), SLLIFRSWANFN (SEQ ID NO:53), SGVVIAT-VIVIT (SEQ ID NO:54), SLGPQGIWGQFN (SEQ ID NO:55), KKSPGRVVGGSV (SEQ ID NO:56), PQGLL-GAPGILG (SEQ ID NO:57), HGPEGLRVGFYESD-VMGRGHARLVHVEEPHT (SEQ ID NO:58), GPQGLAGQRGIV (SEQ ID NO:59), GGSGQRGRKALE (SEQ ID NO:60), SLSALLSSDIFN (SEQ ID NO:61), SLPRFKIIGGFN (SEQ ID NO:62), SLPRFKIIGGFN (SEQ ID NO:63), SLLGIAVPGNFN (SEQ ID NO:64), FFKNIVTPRTPP (SEQ ID NO:65), QVVQLQNYDEED (SEQ ID NO:66), LPIFGESEDNDE (SEQ ID NO:67), QVVTGEAISVTM (SEQ ID NO:68), ALERTFLSFPTN (SEQ ID NO:69), KFQDMLNISQHQ (SEQ ID NO:70), Ala Ala (SEQ.ID.NO.: 71) Ala-Ala-Pro-Val (SEQ.ID.NO.: 72), Ala-Ala-Met (SEQ.ID.NO.: 73) Ala-Ala Pro-Phe (SEQ.ID.NO.: 74), Ala-Ala-Pro-Met (SEQ.ID.NO.: 75), Ala-Ala-Arg (SEQ.ID.NO.: 76) Ser-Ala-Ala-Arg (SEQ.ID.NO.: 77), Ser-Ser-Ala-Ala-Arg (SEQ.ID.NO.: 78), Ser-S carboxyl sugar Ala-Ala-Arg (SEQ.ID.NO.: 79), Ala-Ala-Asp (SEQ.ID.NO.: 80), Ser-Ala-Ala-Asp (SEQ.ID.NO.: 81), Ser-Ser-Ala-Ala-Asp (SEQ.ID.NO.: 82), Arg-Pro-Lys-Pro-Leu-Ala-Nva (SEQ.ID.NO.: 83), Ser Arg-Pro-Lys-Pro-Leu-Ala-Nva (SEQ.ID.NO.: 84), Ser-Ser-Arg-Pro-Lys-Pro-Leu-Ala-Nva (SEQ.ID.NO.: 85), Pro-Cha-Gly-Nva-His-Ala-Dpa-NH.sub.2 (SEQ.ID.NO.: 86), Pro-Leu-Gly-Leu Dpa-Ala-Arg-NH.sub.2 (SEQ.ID.NO.: 87), Pro-Cha-Gly-Nva (SEQ.ID.NO.: 88), Pro-Leu-Gly-Leu (SEQ.ID.NO.: 89), Gly-Pro-Arg (SEQ.ID.NO.: 90), Leu-Pro-Arg (SEQ.ID.NO.: 91), Glu-Gly-Arg (SEQ.ID.NO.: 92), Gly-Pro-Gln-Gly-Ile (SEQ.ID.NO.: 93), or to a peptide of 20 or fewer amino acids in length, wherein the sequence comprises the amino acids: $X_5 X_4 X_3 X_2 X_1$, wherein $X_5$ is from 0 to 16 amino acids; $X_4$ is serine, isoleucine, or lysine; $X_3$ is serine or lysine; $X_2$ is leucine or lysine; and $X_1$ is glutamine, asparagine or tyrosine; or to a oligopeptide that comprises an amino acid sequence selected from: AsnLysIleSerTyrGlnSer (SEQ.ID.NO.: 94), LysIleSerTyrGlnSer (SEQ.ID.NO.: 95), GlyGluAsnGlyValGlnLysAspValSerGlnXaaSerIleTyrSerGlnThrGlu (SEQ.ID.NO.: 96), GlyLysGlyIleSerSerGlnTyrSerAsnThrGluGluArgLeu (SEQ.ID. NO.: 97), AsnLysIleSerTyrTyrSer (SEQ.ID.NO.: 98), AsnLysAlaSerTyrGlnSer (SEQ.ID.NO.: 99), SerTyrGlnSerSer (SEQ.ID.NO.: 100), hArgTyrGlnSerSer (SEQ.ID.NO.: 101), AsnLysIleSerTyrGlnSerAla (SEQ.ID.NO.: 102), AlaAsnLysIleSerTyrTyrSer (SEQ.ID.NO.: 103), AlaAsnLysAlaSerTyrGlnSer (SEQ.ID.NO.: 104), SerTyrGlnSerSerThr (SEQ.ID.NO.: 105), SerTyrGlnSerSerSer (SEQ.ID. NO.: 106), LysTyrGlnSerSerSer (SEQ.ID.NO.: 107), hArgTyrGlnSerSerSer (SEQ.ID.NO.: 108), SerTyrGlnSerSerLeu (SEQ.ID.NO.: 109), wherein hArg is homoarginine and Xaa is any natural amino acid; or a combination thereof.

In an embodiment, of the invention the cleavage recognition site is the cleavage recognition site for a cancer-associated protease. In particular embodiments, the linker amino acid sequence comprises SLLKSRMVPNFN (SEQ.ID.NO.: 44) or SLLIARRMPNFN (SEQ.ID.NO.: 45) cleaved by cathepsin B; SKLVQASASGVN (SEQ.ID.NO.: 46) or SSYLKASDAPDN (SEQ.ID.NO.: 47) cleaved by an Epstein-Barr virus protease; RPKPQQFFGLMN (SEQ.ID. NO.: 48) cleaved by MMP 3 (stromelysin), SLRPLAL-WRSFN (SEQ.ID.NO.: 49) cleaved by MMP-7 (matrilysin); SPQGIAGQRNFN (SEQ.ID.NO.: 50) cleaved by MMP-9; DVDERDVRGFASFL (SEQ.ID.NO.: 51) cleaved by a thermolysin-like MMP; SLPLGLWAPNFN (SEQ.ID.NO.: 52) cleaved by matrix metalloproteinase 2 (MMP-2); SLLIFRSWANFN (SEQ.ID.NO.: 53) cleaved by cathepsin L; SGVVIATVIVIT (SEQ.ID.NO.: 54) cleaved by cathepsin D; SLGPQGIWGQFN (SEQ.ID.NO.: 55) cleaved by matrix metalloproteinase 1 (MMP-1); KKSPGRVVGGSV (SEQ.ID.NO.: 56) cleaved by urokinase-type plasminogen activator; PQGLLGAPGILG (SEQ.ID.NO.: 57) cleaved by membrane type 1 matrixmetalloproteinase (MT-MMP); HGPEGLRVGFYESDVMGRGHARLVHVEEPHT (SEQ.ID.NO.: 58) cleaved by stromelysin 3 (or MMP-11), thermolysin, fibroblast collagenase and stromelysin-1; GPQGLAGQRGIV (SEQ.ID.NO.: 59) cleaved by matrix metalloproteinase 13 (collagenase-3); GGSGQRGRKALE (SEQ.ID.NO.: 60) cleaved by tissue-type plasminogen activator (tPA); SLSALLSSDIFN (SEQ.ID.NO.: 61) cleaved by human prostate-specific antigen; SLPRFKIIGGFN (SEQ.ID.NO.: 62) cleaved by kallikrein (bK3): SLLGIAVPGNFN (SEQ.ID.NO.: 64) cleaved by neutrophil elastase; and FFKNIVTPRTPP (SEQ.ID.NO.: 65) cleaved by calpain (calcium activated neutral protease).

In another embodiment, the cleavage recognition site is the cleavage recognition site for a protease associated with the malaria parasite, *Plasmondium falciparum*. In particular embodiments, the peptide amino acid sequence comprises QVVQLQNYDEED (SEQ.ID.NO.: 66); LPIFGESEDNDE (SEQ.ID.NO.: 67); QVVTGEAISVTM (SEQ.ID.NO.: 68); ALERTFLSFPTN (SEQ.ID.NO.: 69) or KFQDMLNISQHQ (SEQ.ID.NO.: 70). In a another embodiment, the cleavage recognition site is the cleavage recognition site for a viral protease. The linker sequences preferably comprise the sequence Y-X-Y-A-Z wherein X is valine or leucine, Y is a polar amino acid, and Z is serine, asparagine or valine. In particular embodiments, the linker amino acid sequence comprises SGVVNASCRLAN (SEQ.ID.NO.: 27) or SSYVKASVSPEN (SEQ.ID.NO.: 28) cleaved by a human cytomegalovirus protease; SALVNASSAHVN (SEQ.ID. NO.: 29) or STYLQASEKFKN (SEQ.ID.NO.: 30) cleaved by a herpes simplex 1 virus protease; SSILNASVPNFN (SEQ.ID.NO.: 31) cleaved by a human herpes virus 6 protease; SQDVNAVEASSN (SEQ.ID.NO.: 32) or SVYLQASTGYGN (SEQ.ID.NO.: 33) cleaved by a varicella zoster virus protease; or SKYLQANEVITN (SEQ.ID.NO.: 34) cleaved by an infectious laryngotracheitis virus protease. The second moiety sequence containing a cleavage recognition site for a viral protease, wherein the viral protease is selected from the group consisting of: human cytomegalovirus, human herpes virus, varicella zoster virus, hepatitis A virus, hepatitis B virus, hepatitis C virus, Epstein-Barr virus-specific protease, and infectious laryngotracheitis virus. In another embodiment, the cleavage recognition site is the cleavage recognition site for a hepatitis A viral protease. In particular embodiments, the linker amino acid sequence comprises SELRTQSFSNWN (SEQ.ID.NO.: 35) or SELWSQGIDDDN (SEQ.ID.NO.: 36) cleaved by a hepatitis A virus protease. In another embodiment, the cleavage recognition site is the cleavage recognition site for a hepatitis C viral protease. In particular embodiments, the linker amino acid sequence comprises DLEVVTSTWVFN (SEQ.ID.NO.: 37), DEMEE-CASHLFN (SEQ.ID.NO.: 38), EDVVCCSMSYFN (SEQ.ID.NO.: 39) or KGWRLLAPITAY (SEQ.ID.NO.: 40) cleaved by a hepatitis C virus protease. In another embodiment, the cleavage recognition site is the cleavage recognition site for a HIV viral protease VSQNYPIVQNFN (SEQ.ID.NO.: 20); SKARVLAEAMSN (SEQ.ID.NO.: 21); or SIRKILFLDGIN (SEQ.ID.NO.: 22). In another embodiment, the cleavage recognition site is the cleavage recognition site for a HTLV viral protease SAPQVLPVMHPN (SEQ.ID.NO.: 23); SKTKVLWQPKN (SEQ.ID.NO.: 24), SKTKVLVVQPRN (SEQ.ID.NO.: 25) or STTQCFPILHPN (SEQ.ID.NO.: 26). In another embodiment, the cleavage recognition site is the cleavage recognition site for a *Candida* fungal protease. In particular embodiments, the linker amino acid sequence is SKPAKFFRLNFN (SEQ.ID.NO.: 41), SKPIEFFRLNFN (SEQ.ID.NO.: 42) or SKPAEFFAL-NFN (SEQ.ID.NO.: 43) cleaved by *Candida* aspartic protease. In another particular embodiment, the virus is human cytomegalovirus, Epstein-Barr virus, hepatitis virus, herpes virus, human rhinovirus, infectious laryngotracheitis virus, poliomyelitis virus, or varicella zoster virus. In a further particular embodiment, the parasite is *Plasmondium falciparum*.

Collagenase-3 or MMP-13 cleaves peptides containing the amino acid sequences Pro-Cha-Gly-Nva His (SEQ.ID.NO.: 87) and Pro-Leu-Gly-Leu (SEQ.ID.NO.: 88). MMP-2 is involved in regulating tumor cell invasiveness, and cleaves the amino acid sequence Gly-Pro-Gln-Gly-Ile (SEQ.ID.NO.: 89) between the Gly and Ile residues. Human neutrophils also secrete collagenases at sites of inflammation such as MMP-8 (neutrophil collagenase) and MMP-9 (type IV collagenase, 92 kDa gelatinase) (Fosang et al.). Cathepsin G is also secreted from human neutrophils at sites of inflammation; its specificity is greatest for peptides containing the amino acid sequences Ala-Ala-Pro-Phe (SEQ.ID.NO.: 74) or Ala-Ala-Pro-Met (SEQ.ID.NO.: 75). Other enzymes secreted by neutrophils at sites of inflammation include cathepsins B and D as well as lysozyme. Granzymes A and B are secreted by cytotoxic lymphocytes in the synovial fluid of rheumatoid arthritis patients, granzyme A cleaves peptides comprising Gly-Arg and Ala-Ala-Arg (SEQ.ID.NO.: 76) most efficiently, while granzyme B cleaves peptides comprising the amino acid sequence Ala-Ala-Asp (SEQ.ID.NO.: 80).

There are three main human kallikreins, tissue kallikrein (KLK1), glandular kallikrein (KLK2), and APS. PSA shares more extensive homology with KLK2 than with KLK1. Both PSA and KLK2 are produced by prostate epithelial cells and their expression is regulated by androgens. Three amino acid residues were found to be critical for serine protease activity, residues H.sub.65, D.sub.120, and S.sub.213 in PSA. Substrate specificity, described as chymotrypsinogen-like (with KLK2) or trypsin like (with PSA) is thought to be determined by S.sub.207 in PSA and D.sub.209 in KLK2. KLK1 is chymotrypsinogen-like and expressed in the pancreas, urinary system, and sublingual gland. KLK1, like the other kallikreins, is made as a pre-pro-protein and is processed into an active form of 238 amino acids by cleavage of a 24 amino acid terminal signal sequence. A novel prostate-associated kallikrein hereinafter designated HPAK was characterized as having chemical and structural similarity to human pancreatic kallikrein and other kallikreins The KLK and HPAK are contemplated for this invention.

A cleavable peptide is a peptide comprising an amino acid sequence that is recognized by a protease or peptidase or other cleaving agent expressed by a cell and found in surrounding tissue, or produced by a microbe capable of establishing an infection in a mammal. Enzyme-cleavable peptides can, but are not required to, contain one or more amino acids in addition to the amino acid recognition sequence; additional amino acids can be added to the amino terminal, carboxy terminal, or both the amino and carboxy terminal ends of the recognition sequence. Means of adding amino acids to an amino acid sequence, e.g., in an automated peptide synthesizer, as well as means of detecting cleavage of a peptide, e.g., by chromatographic analysis for the amino acid products of such cleavage, are well known to ordinarily skilled artisans given the teachings of this invention. Enzyme-cleavable peptides, typically from about 2 to 20 amino acids in length. Enzyme-cleavable peptides can be modified at their amino termini, for example, so as to increase their hydrophilicity. Increased hydrophobicity enhances exposure of the peptides on the surfaces of lipid-based carriers into which the parent peptide-lipid conjugates have been incorporated. Polar groups suitable for attachment to peptides so as to increase their hydrophilicity are well known, and include, for example and without limitation: acetyl ("Ac"), 3 cyclohexylalanyl ("Cha"), acetyl-serine ("Ac-Ser"), acetyl-seryl-serine ("Ac-Ser-Ser-"), succinyl ("Suc"), succinyl-serine ("Suc-Ser"), succinyl-seryl-serine ("Suc-Ser-Ser"), methoxy succinyl ("MeO Suc"), methoxy succinyl-serine ("MeO-Suc-Ser"), methoxy succinyl-seryl-serine ("MeO-Suc-Ser Ser") and seryl-serine ("Ser-Ser-") groups, polyethylene glycol ("PEG"), polyacrylamide, polyacrylomorpholine, polyvinylpyrrolidine, a polyhydroxyl group and carboxy sugars, e.g., lactobionic, N-acetyl neuraminic and sialic acids, groups. The carboxy groups of these sugars would be linked to the N-terminus of the peptide via an amide linkage. Presently, the preferred N-terminal modification is a methoxy-succinyl modification.

Cell-secreted peptidases which recognize particular amino acid sequences are also well known to ordinarily skilled artisans given the teachings of this invention. Such peptidases include, for example and without limitation: matrix metalloproteinases, serine proteases, cysteine proteases, elastase, plasmin, plasminogen activator, stromelysin, human collagenases, cathepsins, lysozyme, granzymes, dipeptidyl peptidases, peptide hormone-inactivating enzymes, kininases, bacterial peptidases and viral proteases. Elastase, for example, is involved in tumor cell tissue remodeling; the breast cancer cell line MCF-7 has been shown to secrete elastase, the levels of which are inversely correlated to overall survival in breast cancer patients. Moreover, the matrix metalloproteinase, stromelysin-3 ("ST3"), has been localized to the stromal area of tumor cells; it specifically cleaves .alpha.sub.1 proteinase inhibitor between amino acids 350 and 351 (Ala-Met). Stromelysin-1 ("MMP-3") is also localized to areas of tissue remodeling, including sites of inflammation and tumor stroma. Peptidases which hydrolyze enzyme-cleavable peptides also include the group of enzymes that inactivate peptide hormones, e.g., aminopeptidase P and angiotensin-converting enzyme, localized on the surface of endothelial cells. Aminopeptidase P cleaves the Arg-Pro bond in bradykinin, and is localized to lung endothelial cells.

In a further aspect, the invention provides a pharmaceutical composition for treating an infection, such as *Candida*, in a mammal comprising the inhibitor of the invention and a pharmaceutically acceptable carrier, diluent or excipient.

In yet another aspect, the invention provides a method of inhibiting or destroying cells affected by a disease, which cells are associated with a disease specific protease, including cancer or infection with a virus, fungus, or a parasite each of which has a specific protease, comprising the steps of preparing an inhibitor of the invention having a heterologous peptide sequence which contains a cleavage recognition site for the disease-specific protease and administering the inhibitor alone or with an active agent to the cells. In an embodiment, the cancer is T-cell or B-cell lymphoproliferative disease, ovarian cancer, pancreatic cancer, head and neck cancer, squamous cell carcinoma, gastrointestinal cancer, breast cancer, prostate cancer, non small cell lung cancer. In another embodiment, the virus is human cytomegalovirus, Epstein-Barr virus, hepatitis virus, herpes virus, human rhinovirus, human T-cell leukemia virus, infectious laryngotracheitis virus, poliomyelitis virus, or varicella zoster virus. In another embodiment, the parasite is *Plasmondium falciparum*. The present invention also relates to a method of treating a mammal with disease wherein cells affected by the disease are associated with a disease specific protease, including cancer or infection with a virus, fungus, or a parasite each of which has a specific protease by administering an effective amount of one or more inhibitors alone or with an active agent of the invention to said mammal.

In an embodiment, a process is provided for preparing a pharmaceutical for treating a mammal with disease wherein cells affected by the disease are associated with a disease specific protease, including cancer or infection with a virus, fungus, or a parasite each of which has a specific protease comprising the steps of identifying a cleavage recognition site for the protease; preparing an inhibitor wherein the second moiety sequence contains the cleavage recognition site for the protease and suspending the inhibitor in a pharmaceutically acceptable carrier, diluent or excipient and introducing the inhibitor into a vertebrate.

The inhibitors of the invention may be used to specifically inhibit or destroy mammalian cells affected by a disease or infection which have associated with such cells a specific protease, i.e., disease-specific, for example cancer cells or cells infected with a virus, fungus or parasite, all of which are encompassed within the term "disease-specific." It is an advantage of the inhibitors of the invention that they have specificity for said cells without the need for a cell binding component. The specificity of an inhibitor of the invention may be tested by treating the protein with the disease-specific protease which is thought to be specific for the cleavage recognition site and assaying for cleavage products. Disease specific proteases may be isolated from cancer cells or infected cells, or they may be prepared recombinantly. The cleavage products may be identified for example based on size, antigenicity or activity. The ability of the inhibitors of the invention together with an active agent to selectively inhibit or destroy animal cancer cells or cells infected with a virus or parasite may be readily tested in vitro using animal cancer cell lines or cell cultures infected with the virus or parasite of interest. The selective inhibitory effect of the inhibitor of the invention may be determined, for example, by demonstrating the selective inhibition of viral antigen expression in infected mammalian cells, the selective inhibition of general mRNA translation and protein synthesis in diseased cells, or selective inhibition of cellular proliferation in cancer cells or infected cells. Toxicity may also be measured based on cell viability, for example the viability of infected and non-infected cell cultures exposed to the inhibitor may be compared. Cell viability may be assessed by known techniques, such as trypan blue exclusion assays.

In another example, a number of models may be used to test the effect of the inhibitor having a heterologous linker sequence containing a cleavage recognition site for a protease. Determination of invasiveness of human breast cancer cells in vitro can be by measuring tumour cell-mediated proteolysis of extracellular matrix and tumour cell invasion of reconstituted basement membrane (collagen, laminin, fibronectin, Matrigel or gelatin). An in vivo test system involving the implantation of tumours and measurement of tumor growth and metastasis in athymic nude mice has also been described. The effect of inhibitors having a heterologous linker sequence containing a cleavage recognition site for a malarial protease may be tested by a *Plasmodium* invasion assay using human erythrocytes infected with mature-stage merozoite parasites. Alternatively, in vitro cultures of human hepatic parenchymal cells may be used to evaluate schizont infectivity and *Plasmodium* merozoite generation. With respect to models of viral infection and replication, suitable animal cells which can be cultured in vitro and which are capable of maintaining viral replication can be used as hosts. The effect of the inhibitors for infected and non-infected cultures may then be compared. The ability of the inhibitors of the invention to inhibit the expression of these viral antigens may be an important indicator of the ability of the inhibitors/active agent to inhibit viral replication. Levels of these antigens may be measured in assays using labelled antibodies having specificity for the antigens. Inhibition of viral antigen expression has been correlated with inhibition of viral replication (U.S. Pat. No. 4,869,903). Toxicity may also be assessed based on a decrease in protein synthesis in target cells, which may be measured by known techniques, such as incorporation of labelled amino acids, such as [3H] leucine. Infected cells may also be pulsed with radiolabelled thymidine and incorporation of the radioactive label into cellular DNA may be taken as a measure of cellular proliferation. Toxicity may also be measured based on cell death or lysis, for example, the viability of infected and non-infected cell cultures exposed to the inhibitors/ active agent may be compared. Cell viability may be assessed by known techniques, such as trypan blue exclusion assays.

In another example, a number of models may be used to test the effect of the inhibitor having a heterologous linker sequence containing a cleavage recognition site for a protease. Determination of invasiveness of human breast cancer cells in vitro can be by measuring tumour cell-mediated proteolysis of extracellular matrix and tumour cell invasion of reconstituted basement membrane (collagen, laminin, fibronectin, Matrigel or gelatin). An in vivo test system involving the implantation of tumors and measurement of tumor growth and metastasis in athymic nude mice has also been described. The effect of inhibitors having a heterologous linker sequence containing a cleavage recognition site for a malarial protease may be tested by a *Plasmodium* invasion assay using human erythrocytes infected with mature-stage merozoite parasites. Alternatively, in vitro cultures of human hepatic parenchymal cells may be used to evaluate schizont infectivity and *Plasmodium* merozoite generation. With respect to models of viral infection and replication, suitable animal cells which can be cultured in vitro and which are capable of maintaining viral replication can be used as hosts. The effect of the inhibitors for infected and non-infected cultures may then be compared. The ability of the inhibitors of the invention to inhibit the expression of these viral antigens may be an important indicator of the ability of the inhibitors/active agent to inhibit viral replication. Levels of these antigens may be measured in assays using labeled antibodies having specificity for the antigens. Inhibition of viral antigen expression has been correlated with inhibition of viral replication (U.S. Pat. No. 4,869,903). Toxicity may also be assessed based on a decrease in protein synthesis in target cells, which may be measured by known techniques, such as incorporation of labeled amino acids, such as [3H] leucine. Infected cells may also be pulsed with radiolabeled thymidine and incorporation of the radioactive label into cellular DNA may be taken as a measure of cellular proliferation. Toxicity may also be measured based on cell death or lysis, for example, the viability of infected and non-infected cell cultures exposed to the inhibitors/active agent may be compared. Cell viability may be assessed by known techniques, such as trypan blue exclusion assays.

In one embodiment, said active agent is preferably a cell-penetrating or cell membrane-associating moiety. Discovery that attachment of a cell-penetrating or cell membrane-associating moiety to peptides derived from a GPCR produces agonists and/or antagonists of receptor-G protein signaling was made. These modified peptides—termed pepducins—exhibit selectivity for their cognate receptor. Pepducins for protease-activated receptors (PARs), e.g., PAR1, PAR2, and PAR4, cholecystokinins A and B (CCKA, CCKB), somatostatin-2 (SSTR2), melanocortin-4 (MC4R), glucagon-like peptide-1 receptor (GLP-1R), and P2Y.sub.12 ADP receptor are agonists and/or antagonists for the receptors from which they are derived. These compositions are useful to activate or inhibit the activity of a broad range of GPCRs. Human PARs include PAR1; PAR2; PAR3; and PAR4.

In addition to peptide-based inhibitors and pepducins, the invention encompasses compositions in which the peptide contains a peptidomimetic. For example, the invention includes peptide compounds in which one or more peptide bonds have been replaced with an alternative type of covalent bond, which is not susceptible to cleavage by peptidases (a "peptide mimetic" or "peptidomimetic"). Where proteolytic degradation of peptides following injection into the subject is a problem, replacement of a particularly sensitive peptide bond with a noncleavable peptide mimetic renders the resulting peptide more stable and thus more useful as a therapeutic. Such mimetics, and methods of incorporating them into peptides, are well known in the art. Similarly, the replacement of an L-amino acid residue (e.g., with a D-amino acid) renders the peptide less sensitive to proteolysis. Additionally, peptide compounds of the invention can be synthesized as retro-inverso isomers, which include peptides of reverse sequence and chirality. The net result of combining D-enantiomers and reverse synthesis is that the positions of carbonyl and amino groups in each amide bond are exchanged, while the position of the side-chain groups at each alpha carbon is preserved. For example, if the peptide model is a peptide formed of L-amino acids having the sequence ABC, the retro-inverso peptide analog formed of D-amino acids would have the sequence CBA. The procedures for synthesizing a chain of D-amino acids to form the retro-inverso peptides are known in the art. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

In preferred embodiment of this invention, the inhibitor can be an antibody molecule or the epitope binding moiety of an antibody molecule and the like. Antibodies provide high binding avidity and unique specificity to a wide range of target antigens and haptens. Monoclonal antibodies useful in the practice of the present invention include whole antibody and fragments thereof and are generated in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. Human monoclonal antibodies or "humanized" murine antibody are also used in accordance with the present invention. For example, murine monoclonal antibody may be "humanized" by genetically recombining the nucleotide sequence encoding the murine Fv region (i.e., containing the antigen binding sites) or the complementarity determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction in the possibility of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarity determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv phage library.

Limitation of scFv molecules is their monovalent interaction with target antigen. One of the easiest methods of improving the binding of a scFv to its target antigen is to increase its functional affinity through the creation of a multimer. Association of identical scFv molecules to form diabodies, triabodies and tetrabodies can comprise a number of identical Fv modules. These reagents are therefore multivalent, but monospecific. The association of two different scFv molecules, each comprising a VH and VL domain derived from different parent Ig will form a fully functional bispecific diabody. A unique application of bispecific scFvs is to bind two sites simultaneously on the same target molecule via two (adjacent) surface epitopes. These reagents gain a significant avidity advantage over a single scFv or Fab fragments. A number of multivalent scFv-based structures has been engineered, including miniantibodies, dimeric miniantibodies, minibodies, (scFv)2, diabodies and triabodies. These molecules span a range of valence (two to four binding sites), size (50 to 120 kDa), flexibility and ease of production. Single chain Fv antibody fragments (scFvs) are predominantly monomeric when the VH and VL domains are joined by polypeptide linkers of at least 12 residues. The monomer scFv is thermodynamically stable with linkers of 12 and 25 amino acids length under all conditions. The noncovalent diabody and triabody molecules are easy to engineer and are produced by shortening the peptide linker that connects the variable heavy and variable light chains of a single scFv molecule. The scFv dimers are joined by amphipathic helices that offer a high degree of flexibility and the miniantibody structure can be modified to create a dimeric bispecific (DiBi) miniantibody that contains two miniantibodies (four scFv molecules) connected via a double helix. Gene-fused or disulfide-bonded scFv dimers provide an intermediate degree of flexibility and are generated by straightforward cloning techniques adding a C-terminal Gly4Cys sequence. scFv-CH3 minibodies are comprised of two scFv molecules joined to an IgG CH3 domain either directly (LD minibody) or via a very flexible hinge region (Flex minibody). With a molecular weight of approximately 80 kDa, these divalent constructs are capable of significant binding to antigens. The Flex minibody exhibits impressive tumor localization in mice. Bi- and tri-specific multimers can be formed by association of different scFv molecules. Increase in functional affinity can be reached when Fab or single chain Fv antibody fragments (scFv) fragments are complexed into dimers, trimers or larger aggregates. The most important advantage of multivalent scFvs over monovalent scFv and Fab fragments is the gain in functional binding affinity (avidity) to target antigens. High avidity requires that scFv multimers are capable of binding simultaneously to separate target antigens. The gain in functional affinity for scFv diabodies compared to scFv monomers is significant and is seen primarily in reduced off-rates, which result from multiple binding to two or more target antigens and to rebinding when one Fv dissociates. When such scFv molecules associate into multimers, they can be designed with either high avidity to a single target antigen or with multiple specificities to different target antigens. Multiple binding to antigens is dependent on correct alignment and orientation in the Fv modules. For full avidity in multivalent scFvs target, the antigen binding sites must point towards the same direction. If multiple binding is not sterically possible then apparent gains in functional affinity are likely to be due the effect of increased rebinding, which is dependent on diffusion rates and antigen concentration. Antibodies conjugated with moieties that improve their properties are also contemplated for the instant invention. For example, antibody conjugates with PEG that increases their half-life in vivo can be used for the present invention. Immune libraries are prepared by subjecting the genes encoding variable antibody fragments from the B lymphocytes of naive or immunized animals or patients to PCR amplification. Combinations of oligonucleotides which are specific for immunoglobulin genes or for the immunoglobulin gene families are used. Immunoglobulin germ line genes can be used to prepare semisynthetic antibody repertoires, with the complementarity-determining region of the variable fragments being amplified by PCR using degenerate primers. These single-pot libraries have the advantage that antibody fragments against a large number of antigens can be isolated from one single library. The phage-display technique can be used to increase the affinity of antibody fragments, with new libraries being prepared from already existing antibody fragments by random, codon-based or site-directed mutagenesis, by shuffling the chains of individual domains with those of fragments from naive repertoires or by using bacterial mutator strains.

In preferred embodiment of this invention, the phage-display technique can also be used to select for the inhibitors. In the phage-display the antigen-binding domains, peptides, or inhibitors are cloned, as fusions with the coat protein g3P of filamentous bacteriophages. Antigen-binding phages are selected on antigen-loaded plastic vessels (panning), on antigen-conjugates, paramagnetic beads or by binding to cell surfaces.

Although the primary specificity of the inhibitors of the invention for diseased cells is mediated by the specific cleavage of the cleavage recognition site, second moiety, it will be appreciated that specific binding components may optionally be conjugated to the inhibitors of the invention. Such binding components may be expressed as fusion proteins with the proteins of the invention or the cell binding component may be physically or chemically coupled to the inhibitors component. Examples of suitable cell binding components include antibodies to cancer, viral or parasitic proteins. The term "antibody" as used herein is intended to include fragments thereof which also specifically react with a cell surface component. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments. Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Alternatively, a SCID-hu mouse, for example the model developed by Genpharm, can be used to produce antibodies, or fragments thereof. In one embodiment, a new type of high avidity binding molecule, termed peptabody, created by harnessing the effect of multivalent interaction is contemplated. A short peptide ligand was fused via a semirigid hinge region with the coiled-coil assembly domain of the cartilage oligomeric matrix protein, resulting in a pentameric multivalent binding molecule. In preferred embodiment of this invention, ligands and/or chimeric inhibitors can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. Alternatively, two or more active agents and or inhibitors attached to targeting moieties can be administered, wherein each conjugate includes a targeting moiety, for example, a different antibody. Each antibody is reactive with a different target site epitope (associated with the same or a different target site antigen). The different antibodies with the agents attached accumulate additively at the desired target site. Antibody-based or non-antibody-based targeting moieties may be employed to deliver a ligand or the inhibitor to a target site. Preferably, a natural binding agent for an unregulated antigen is used for this purpose. For example, diseases such as hepatoma or myeloma are generally characterized by unregulated IL-6 receptors for which IL-6 acts as an autocrine or paracrine moiety with respect to rapid proliferation of these target cell types. For the treatment of such ailments, IL-6 may therefore be employed as a targeting moiety in a targeting protocol of the present invention.

The inhibitors of the invention may be formulated into pharmaceutical compositions for administration to subjects in a biologically compatible form suitable for administration in vivo. By biologically compatible form suitable for administration in vivo is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The active substance may be administered in a convenient manner such as by injection (subcutaneous, intravenous, intramuscular, etc.), oral administration, inhalation, transdermal administration (such as topical cream or ointment, etc.), or suppository applications. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. On this basis, the compositions include, albeit not exclusively, solutions of the substances in association with one or more pharmaceutically acceptable vehicles or diluents, and contained in buffered solutions with a suitable pH and iso-osmotic with the physiological fluids.

For example, new technology for the local and sustained delivery of immunostimulatory molecules to the tumor environment for cancer immunotherapy was evaluated. The ability of cytokines delivered by biodegradable microspheres to promote the antitumor activity of human peripheral blood lymphocytes (PBL) was tested in a human PBL, human tumor, and SCID mouse (SCID-Winn) model. Co engraftment of human recombinant IL-12-loaded microspheres with human PBL and tumors in SCID mice promoted complete tumor suppression in as many as 100% of the mice.

The pharmaceutical compositions may be used in methods for treating animals, including mammals, preferably humans, with cancer or infected with a virus or a parasite. It is anticipated that the compositions will be particularly useful for treating patients with a cancer, B-cell lymphoproliferative disease, (melanoma), mononucleosis, cytomegalic inclusion disease, malaria, herpes, shingles, hepatitis, poliomyelitis, or infectious laryngotracheitis. The dosage and type of recombinant protein to be administered will depend on a variety of factors which may be readily monitored in human subjects. Such factors include the etiology and severity (grade and stage) of neoplasia, the stage of malarial infection (e.g. exoerythrocytic vs. erythrocytic), or antigen levels associated with viral load in patient tissues or circulation.

As mentioned above, the novel inhibitors of the present invention are useful in treating cancerous or infected cells wherein the cells contain a specific reagent that can cleave the linker region of the inhibitor. Method of treatment usually consists of contacting the cell with the inhibitor alone or together with an active agent. The contact is not always a physical contact, the inhibitor can be for example in the vicinity of a target cell. Different administration routes can accomplish such contact. One skilled in the art can appreciate that many different inhibitors can be prepared once a disease associated protease has been identified. For example, the novel inhibitors molecules of the invention may be used to treat CNS tumors. Increased activity of Insulin-type Growth Factor Binding Protein-3 (IGFBP-3) protease in the Cerebral Spinal Fluid of patients with CNS tumors was described. Prostate-specific antigen (PSA) is an IGFBP-3 protease. Cathepsin D is IGFBP-3 protease. Another example of a specific use of the invention is treatment of human glioma which has been shown to produce cathepsin D. In addition, the novel inhibitors of the present invention may be used to treat cystic fibrosis. CF airway disease is characterized by neutrophil-dominated chronic inflammation with an excess of uninhibited neutrophil elastase (NE). NE levels in CF sputum are 350 times higher than that found in normal sputum. The novel inhibitors of the present invention may also be used to treat multiple sclerosis. Cathepsin B (possibly from inflammatory cells of hematogenous origin) is implicated in the demyelination found in multiple sclerosis.

In one embodiment, said vertebrate cells are preferably mammalian and even more preferably human cells. These cells are preferably tumor cells, muscle cells, epithelial cells, leukemia cells, virus-infected cells, endothelial cells, cells adjoining activated endothelial cells, activated or proliferating endothelial cells, tumor cells, muscle cells, smooth muscle cells, fibroblasts, macrophages, lymphocytes, liver cells, kidney cells, synovial cells, joint cells, inflammatory cells, virus-infected cells, bacteria-infected cells, parasite-infected cells, bronchial epithelial cells, glia cells, or leukemia cells, B lymphocytes, glia cells, or synovial cells. Enzymes are preferably released by tumor cells, by diseased cells and by cells which are involved in an inflammatory process and the like. Inflammatory diseases include but are not limited to multiple sclerosis, autoimmune arthritis, and other immune diseases.

In preferred embodiment of this invention, the inhibitor can be constructed from IL-4 receptor. For example, it has been shown that soluble forms of the IL-4 receptor molecules (sIL-4R) act as a transporter molecule for IL-4 from the site of production to other compartments of the immune system. IL-4 that dissociates from sIL-4R retains its bioactivity. Recombinant forms of human sIL-4R prolong IL-4 half-life and neutralize IL-4 in vitro and in vivo without mediating cellular activation. IL-4 effects are modulated by soluble receptor molecules. Recombinant soluble IL-4R is a 54 kilodalton glycoprotein consisting of the extracellular domain of the human IL-4 receptor lacking the transmembrane and cytoplasmic domains. IL-4 binds with high affinity and specificity to the sIL 4R alpha chain. The affinity is comparable to membrane-bound receptor. Soluble human IL-4 receptors are exclusively produced by proteolytic cleavage of the cell surface receptor and are present in biological fluids.

In preferred embodiment of this invention, the inhibitor can be an inhibitor of circularly permuted chemokine or a taxin fusion with such chemokine. The IL-4 toxin (called IL4(38-37)-PE38KDEL, or cpIL4-PE, or IL-4-PE) contains circularly permuted IL-4 mutant in which amino acids 38-129 were linked to amino acids 1-37 via a linker peptide GGNGG (SEQ ID NO: 112) and fused to the amino terminus of truncated Pseudomonas exotoxin (PE), consisting of amino acids 253-364 and 381-608, followed by KDEL (SEQ ID NO: 113) (an endoplasmic retaining sequence), at positions 609-612. This recombinant toxin is preferable to native IL-4 fusion toxin because the new ligand-toxin junction results in improved IL-4 receptor binding. Pseudomonas exotoxin is a powerful bacterial toxin that is highly cytotoxic to IL-4R-positive tumor cells in vitro and in vivo.

In preferred embodiment of this invention, the inhibitor can be constructed from TNF receptor. For example, recombinant dimers of TNF receptors have up to 4,000 fold higher affinity for TNF over the soluble monomeric counterparts. These dimers can be used in substantially lower concentrations to achieve a similar degree of TNF binding and have longer half-life in vivo TNF has been reported to have certain anti-cancer activity. In particular, the effects of TNF in certain cancer treatments have been reported. TNF, for example, has been described as having certain protective effects against radiation under particular experimental conditions. U.S. Pat. No. 5,747,023 discloses the use of TNF in the treatment of radiation damage. The effect of TNF in protecting bone marrow precursor cells from irradiation has also been described. TNF alpha is a naturally occurring secreted protein with clinical antitumor activity. Preclinical studies have shown that TNF alpha delivered by gene therapy and used in combination with radiation treatment, disrupts the tumor's blood vessels resulting in rapid necrosis of the tumor. TNF receptor-bearing cells include adipocytes, myotubes, cervical carcinoma, fetal lung, bladder carcinoma, histocytic leukemia, erythroleukemia, promyelocytic leukemia, epidermoid carcinoma, cervical carcinoma, T lymphoma, human lymphocytes, lymphoblastic leukemia (two receptors), monocytic leukemia, foreskin fibroblast, connective tissue (two receptors), murine macrophage, and bovine endothelium. There are high, intermediate and low affinity TNF receptors. Gamma-interferon-activated monocytes are cytotoxic leukemia or sarcoma target cells. Pretreatment of monocytes with recombinant TNF-alpha for 1 hour leads to increased killing of tumor cells. In preferred embodiment of this invention, the inhibitor may be constructed from TNF-related apoptosis-inducing ligand (TRAIL) and its receptors that include four distinct receptors that interact with a single ligand. Currently, these molecules are of major interest due to their potential roles and application in cancer therapy. Studies with soluble TRAIL have found multimeric, or cross-linked, versions to be more effective at inducing apoptosis than monomeric TRAIL. In addition, these early studies identified two other unique characteristics of TRAIL. TRAIL induces apoptotic cell death only in tumorigenic or transformed cells and not in normal cells.

In preferred embodiment of this invention, the inhibitor may be used in treatment of autoimmune diseases such as rheumatoid arthritis, systemic lupus erythematosus, insulin-dependent diabetes mellitus, multiple sclerosis, pulmonary fibrosis and the like, and tissue transplantation facilitation in liver and kidney tissues, for example, obviation or prevention of graft-versus-host reaction, and the like.

In preferred embodiment of this invention, the inhibitor interacts, binds, or inhibits a ligand. Examples of ligands which can interact with chimeric inhibitors are growth factors such as VEGF, PDGF, EGF, TGF alpha, TGF beta, KGF, SDGF, FGF, IGF, HGF, NGF, BDNF, neurotrophins, BMF, bombesin, M-CSF, GM-CSF, thrombopoietin, erythropoietin, SCF, SDGF, oncostatin, PDEGF or endothelin-1, antibodies, cytokines, such as IL-1, IL-2, IL-3, IL-4, IL-5, IL-6, IL-7, IL-8, IL-9, IL-10, IL-11, IL-12, IL-13, IL-14, IL-15, interferons alpha, beta and gamma, (IFN), tumor necrosis factors TNF alpha, and TNF beta, lymphotoxin alpha, chemokines, such as RANTES, MCAF, MIP-1alpha or MIP-1beta, NAP or beta-thromboglobulin, immunosuppressive cytokines, such as TGF-beta, kinases involved in cell membrane receptor activation, signal transduction and cell cycle control or programmed cell death, kinase inhibitors, dual specificity kinases also known as MAP kinases, MAP (mitogen-activated protein) kinase (MAPK), peptide hormones, such as SRH, SIH or STH, MRH or MSH, PRH, HE or prolactin, LH-RH, FSH-RH, LH/ICSH or FSH, TRH or TSH, CRH or ACTH, matrix metalloelastase, elastase, proteins and factors involved in angiogenesis, angiotensin, kinins, homologs or analogs thereof, or vitamins, such as folic acid, muteins of the above and the like.

According to the present invention, a recognition domain or a ligand can be an adhesion molecule, a part of an adhesion molecule or an analog of an adhesion molecule which binds to a corresponding adhesion molecule which is located in the cell membrane or to another specific binding structure for an adhesion molecule on the target cell or in the extracellular matrix or a virus coat protein, or a part of a coat protein. Examples of such adhesion molecules which are capable of functioning as ligands are Lewis X (for GMP-140), S Lewis X (for ELAM-1), LFA-1 (for ICAM-1 and ICAM-2), MAC-1 (for ICAM-1), VLA-4 (for VCAM-1), PECAM (for PECAM), vitronectin (for the vitronectin receptor), GMP-140 (for Lewis X), S Lewis X (for ELAM-1), ICAM-1, ICAM-2 (for LFA-1 and MAC-1), VCAM-1 (for VLA-4), fibronectin (for VLA-4), laminin (for VLA-6), laminin (for VLA-1, VLA-2 and VLA-3), fibrinogen (for GPIIb-IIIa), B7 (for CD28), CD28 (for B7), CD40 (for CD40L) or CD40L (for CD40), muteins of the above and the like.

In preferred embodiment of this invention, the inhibitors of present invention interact with a coagulation factor selected from the group consisting of thrombin, factor Va, factor VIIa, factor IXa, factor Xa, TF coagulation-active fragments and factor XIIa; thrombin which is mutated in the region of the Arg-Thr cleavage site at amino acid position 327/328; a fibrinolytic protein selected from the group consisting of urokinase, tPA and functional hybrids thereof; a complement factor selected from the group consisting of CVF, C3b and functional cleavage products thereof; an antithrombotic protein selected from the group consisting of protein C, C-1S inhibitor, alpha1-antitrypsin, hirudin, TFPI, PAI 1, PAI-2 and PAI-3; a kallikrein; a cytostatic, cytotoxic or inflammation-eliciting protein; an antiangiogenic protein; an immunomodulatory protein; an antiinflammatory protein; a protein which relieves damage to the nervous system; a protein which relieves the neurotoxic effect of TNFalpha; an angiogenesis-stimulating protein; a hypotensive protein; an antiviral protein; a cytokine; an interferon; a tumor necrosis factor; oncostatin M or LIF; a cytokine receptor; the moiety of a cytokine receptor which is external to the cell; a cytokine antagonist; a growth factor; a growth factor receptor; the moiety of a growth factor receptor which is external to the cell; angiostatin; platelet factor 4; TIMP-1, TIMP-2 or TIMP-3; a nitroreductase; a beta-glucuronidase; a carboxypeptidase; a beta-lactamase; a cytosine deaminase; a catalase; a peroxidase; a phosphatase; an oxidase; kallikrein; an endothelial cell nitric oxide synthase, muteins of the above or the like.

In preferred embodiment of this invention, the inhibitor interacts, binds, inhibits other anti-tumor agents that may be delivered in accordance with the targeting techniques of the present invention for example selectins, including L-selectin, P-selectin and E-selectin. The presence of cytokines stimulates cells, such as endothelial cells, to express selectins on the surfaces thereof. Selectins bind to white blood cells and aid in delivering white blood cells where they are needed.

In preferred embodiment of this invention, the inhibitor interacts, binds, inhibits a toxin. Toxins in this regard include holotoxins, such as abrin, ricin, modeccin, *Pseudomonas* exotoxin A, Diphtheria toxin, pertussis toxin and Shiga toxin; and A chain or "A chain-like" molecules, such as ricin A chain, abrin A chain, modeccin A chain, the enzymatic portion of *Pseudomonas* exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides. Ribosomal inactivating proteins (RIPs), naturally occurring protein synthesis inhibitors that lack translocating and cell-binding ability and other highly toxic agents, and the like, are also contemplated for use in the practice of the present invention. Such extremely highly toxic molecules exhibit toxicities at micromolar and picomolar concentrations. For example, palytoxin molecules having a preserved free terminal amino group are approximately 500-fold more toxic than palytoxin derivatives lacking such a free amine. Other examples of membrane active drugs are amphotericin B, polymyxin B, muteins of the above and the like.

In preferred embodiment of this invention, the inhibitor interacts, binds, inhibits a drug which include, in general, alkylating agents, antiproliferative agents, tubulin binding agents and the like. The meaning drug includes any chemical therapeutic molecule used to treat a disease, preferably human disease. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. Other useful cytotoxic agents include estramustine, cisplatin and cyclophosphamide. One skilled in the art may make chemical modifications to the desired compound in order to make reactions of that compound more convenient for purposes of preparing conjugates of the invention. The most highly preferred drugs are the anthracycline antibiotic agents. One skilled in the art understands that drug formula includes compounds which are drugs, or are derivatives of drugs, which have acquired in the art different generic or trivial names.

In preferred embodiment of this invention, the inhibitor, a ligand which interacts, inhibits, binds with the inhibitor, or both can be specifically targeted to desired site by a targeting moiety. Targeting to the target tissues may be accomplished, for instance, via antibodies directed to tumor specific antigens, such that the inhibitor-ligand complexes are presented, for instance, to the infiltrating monocyte population in a localized environment. Ligands need to be taken close to a target cell to exert a cytotoxic effect. In the case of targeting moiety-ligand conjugates, it would be advantageous to combine the relative target specificity of a targeting moiety and specific ligand release by the inhibitor.

Preferred targeting moieties of the present invention include antibodies (polyclonal or monoclonal), antibody fragments, peptides, oligonucleotides, hormones, or the like. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) and homing peptides are also preferred targeting moieties. Also, anti-EGF receptor antibodies, which internalize following binding to the receptor and traffic to the nucleus to an extent, are preferred targeting moieties for use in the present invention to facilitate delivery of an inhibitor-ligand. Examples of these receptor include but are not limited to a cytokine receptor, a growth factor receptor; a Fc receptor, a receptor or of a viral glycoprotein, or a glycophospholipid anchor, VEGF receptor, hormone receptor, IL-1 receptor, IL-1 alpha receptor, IL-1beta receptor, IL-2 receptor, IL-3 receptor (alpha subunit), IL-3 receptor (beta subunit), IL-4 receptor, IL-6 receptor, IFN gamma receptor, IL-7 receptor, IL-8 receptor, IL-9 receptor, IL-10 receptor, IL-11 receptor, GM-CSF receptor, IL-12 receptor, IL-13 receptor, LIF receptor, macrophage colony stimulating factor (M-CSF) receptor, granulocyte macrophage colony stimulating factor (GM-CSF), the moiety of a cytokine receptor which is external to the cell, a receptor-binding part sequence of these ligands the extracellular moiety of an Fc receptor, type I and II macrophage scavenger receptors, MAC-1 (leukocyte function antigen) receptor, LFA-1 alpha (leukocyte function antigen) receptor or p150,95 (leukocyte function antigen) receptor. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population and the like may also be used within the claimed invention. In addition, synthetic targeting moieties may be designed.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety target cell binding. Another targeting moiety functional equivalent is a short polypeptide designated as a "minimal" polypeptide, constructed for example by using computer-assisted molecular modeling and mutants having altered binding affinity, which minimal polypeptides exhibit the binding affinity of the targeting moiety.

In conventional targeted therapy, an active agent can be bound to an antibody or other targeting moiety to form the diagnostic or therapeutic conjugate to be administered. The accretion of active agent to target sites is therefore dictated by the pharmacokinetics of the targeting moiety. Whole monoclonal antibodies, for example, generally require about 20-72 hours to achieve optimal target site accretion, while antibody fragments such as Fab and Fab' fragments generally require about 0-8 hours and F(ab') fragments generally require about 8-24 hours. Consequently, the conjugate recipient's normal tissues are exposed to the active agent for the accretion time, leading to undesirable normal tissue toxicity. As a result of this normal tissue exposure, extremely highly toxic moieties cannot generally be employed in targeted therapy. Such phenomena is circumvented by use of the inhibitor of instant invention.

In preferred embodiment of this invention, the inhibitor the oligopeptides, peptide subunits and peptide derivatives (also termed "peptides"), a lipid, a carbohydrate, a polysaccharide, a glycolipid, a nucleic acid, or a conjugate of the above of the present invention can be synthesized from their constituent amino acids by conventional peptide synthesis techniques, preferably by solid-phase technology or from appropriate building blocks, for example sugars, triglycerides, lipids, nucleotides etc. The peptides are then purified by reverse-phase high performance liquid chromatography (HPLC). The conjugates of the instant invention which comprise the oligopeptide containing the cleavage site may similarly be synthesized by techniques well known in the medicinal chemistry art. For these purposes a reagent such as a combination of 2-(1H-benzotriazol-1-yl)-1,3,3-tetramethyluronium hexafluorophosphate (known as HBTU) and 1-hydroxybenzotriazole hydrate (known as HOBT), dicyclohexylcarbodiimide (DCC), N-ethyl-N-(3-dimethylaminopropyl)-carbodiimide (EDC), diphenylphosphorylazide (DPPA), benzotriazol-1-yl-oxy-tris(dimethylamino)phosphonium hexafluorophosphate (BOP) and the like may be utilized. Furthermore, the instant inhibitor conjugate may be formed by a non-peptidyl bond. For example, an agent may be covalently attached to the carboxyl terminus of the oligopeptide via a hydroxyl moiety on the agent, thereby forming an ester linkage. For this purpose a reagent such as a combination of HBTU and HOBT, a combination of BOP and imidazole, a combination of DCC and DMAP, and the like may be utilized. The carboxylic acid may also be activated by forming the nitrophenyl ester or the like and reacted in the presence of DBU (1,8-diazabicyclo[5,4,0]undec-7-ene. The instant conjugate may also be formed by attachment of the oligopeptide to the agent via a linker unit. Such linker units include, for example, a biscarbonyl alkyl diradical whereby an amine moiety on the cytotoxic agent is connected with the linker unit to form an amide bond and the amino terminus of the oligopeptide is connected with the other end of the linker unit also forming an amide bond. Other such linker units which are stable to the physiological environment but are cleavable upon a hydrolytic cleavage, are also envisioned. Furthermore, linker units may be utilized that, upon cleavage of the cleavage site, remain attached to the agent but do not significantly decrease the cytotoxic activity of such a post-cleavage cytotoxic agent derivative when compared with an unmodified cytotoxic agent. One skilled in the art understands that in the synthesis of compounds of the invention, one may need to protect or block various reactive functionalities on the starting compounds and intermediates while a desired reaction is carried out on other portions of the molecule.

In preferred embodiment of this invention, the inhibitor or nucleic acid encoding the inhibitor of this invention can be administered locally (e.g. onto the skin), nasally, orally, gastrointestinally, intrabronchially, intravesically, intravaginally, into the uterus, sub-cutaneously, intramuscularly, peri-articularly, intraarticularly, into the cerebrospinal fluid, into the brain tissue, into the spinal medulla, into wounds, intraperitoneally or intrapleurally, or systemically, e.g. intravenously, intraarterially, intraportally or into the heart. An intravenously administered agent becomes bioavailable faster than an agent administered via other routes, therefore generally rendering intravenous administered agents more toxic. Alternatively, intraarterial administration of agents of instant invention can be applied to disease targets present in organs or tissues for which supply arteries are accessible. For example, applications for intraarterial delivery of the present invention include treatment of liver tumors through hepatic artery administration, brain primary tumors and metastases through carotid artery administration, lung carcinomas through bronchial artery administration and kidney carcinomas through renal artery administration. Intraarterial administration targeting can be conducted using inhibitors of instant invention alone or in combination with lymphokines, such as IL-2 and tumor necrosis factor, gamma-interferon, or lymphokine/inhibitor-loaded liposomes which are examples of active agents useful for the delivery thereof in the practice of this embodiment of the present invention.

In preferred embodiment of this invention, the inhibitor and/or ligand could be incorporated into a biodistribution directing moiety, such as a polymer, to direct the biodistribution of the inhibitor alone or inhibitor-active agent to proximity of desired target or to allow for continuous release of thereof. Alternatively, microparticulate or nanoparticulate polymeric bead dosage forms may be employed. In this case, the inhibitor or inhibitor and active agent will be encapsulated in the particulate dosage forms which have a number of ligand or anti-ligand molecules bound thereon. In this manner, inhibitor or inhibitor and active agent are release at that site over time to provide a sustained therapeutic benefit. These sustained release dosage forms are also useful with regard to other active agents useful in the practice of the present invention, such as cytokines, toxins, chemotherapeutic agents, and the like. Release of the active agent from the particulate dosage forms of the present invention can occur as a result of both diffusion and particulate matrix erosion. Biodegradation rate directly impacts active agent release kinetics. Controlled release parenteral formulations of the inhibitor compositions of the present invention can be made as implants, oily injections, or as particulate systems. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Liposomes can be used for controlled release as well as drug targeting of entrapped drug.

One embodiment of the present invention is in the area of photodynamic therapy. The inhibitor of the present invention can bind or inhibit a photosensitizing agent that absorbs a certain wavelength of light is administered to the recipient and localizes to the target site and target cells are illuminated with a light source of the appropriate wavelength. When the photosensitizing agent absorbs the light, it transfers the absorbed energy to oxygen molecules dissolved in the tissue producing an active oxygen molecules which destroy cells in the vicinity of the target cells where the agent has been localized. In the practice of the present invention, targeting of a selective site is facilitated by the inhibitor binding the photosensitizing agent and following enzymatic cleavage of the inhibitor at the target site the agent is released. Common photosensitizing agents are porphyrin derivatives with a strong absorption band between 600 and 700 nm. Chemical modification of porphyrin compounds is undertaken to enhance performance of those compounds in photodynamic therapy protocols.

In preferred embodiment of this invention, the inhibitor also provides a method of determining PSA activity in a PSA-containing sample, comprising contacting the sample with a detectably labeled inhibitor containing a peptide which is specifically cleaved by PSA for a period of time sufficient to allow PSA to cleave the inhibitor, detecting the detectable label to yield a detection level, which is then compared to the detection level obtained by contacting the same detectably labeled inhibitor with a standard PSA sample of known activity.

The one or more inhibitor candidates can be tested with any of a number of cell-based assays that elicit detectable signals in proportion to the efficacy of the inhibitor. Conveniently, the candidates are incubated with cells in multi-well plates, and the biological effects are measured via a signal (e.g., fluorescence, reflectance, absorption, or chemiluminescence) that can be quantitated using a plate reader. Alternatively, the incubation mixtures can be removed from the wells for further processing and/or analysis. The structures of active and optionally inactive compounds, if not already known, are then determined, and this information can be used to identify lead compounds and to focus further synthesis and screening efforts. Other examples include assays directed to inhibiting cell signaling, such as IL-4 receptor inhibition; assays for blocking cellular proliferation, and gene expression assays. In a typical gene expression assay, a gene of interest is placed under the control of a suitable promoter and is followed downstream by a gene for producing a reporter species such as .beta.-galactosidase or firefly luciferase. An inhibitory effect can be detected based on a decrease in reporter signal.

In preferred embodiment of this invention the inhibitor is used in combination with chemotherapy, combination biochemotherapy, or other therapy. It can be used as a standalone or as adjuvant to other treatments such as cancer chemotherapy, radiation therapy, or hormonal therapy for immune diseases. The treatment could be used for advanced metastatic cancers as well as for newly diagnosed cancer, residual disease, recurrent disease, or as prophylactic therapy, for instance, for completely resected tumors. Compositions and methods of the present invention have particular utility in the area of human and veterinary therapeutics. Generally, administered dosages will be effective to deliver picomolar to micromolar concentrations of the therapeutic composition to the effector site. Appropriate dosages and concentrations will depend on factors such as the therapeutic composition or drug, the site of intended delivery, and the route of administration, all of which can be derived empirically according to methods well known in the art. Further guidance can be obtained from studies using experimental animal models for evaluating dosage, as are known in the art.

Administration of the compounds of the invention with a suitable adjuvant, a pharmaceutically acceptable carrier, a diluent, or a pharmaceutical excipient as necessary can be carried out via any of the accepted modes of administration. Thus, administration can be, for example, intravenous, topical, subcutaneous, transcutaneous, intramuscular, oral, intrajoint, perenteral, peritoneal, intranasal, or by inhalation. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages. The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art. For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]). Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema. If desired, the composition to be administered may also contain minor amounts of non-toxic auxiliary substances such as wetting or emulsifying agents, pH buffering agents, such as, for example, sodium acetate, sorbitan monolaurate, or triethanolamine oleate. For topical administration, the composition is administered in any suitable format, such as a lotion or a transdermal patch. For delivery by inhalation, the composition can be delivered as a dry powder (e.g., Inhale Therapeutics) or in liquid form via a nebulizer. Methods for preparing such dosage forms are known or will be apparent to those skilled in the art; for example, see Remington's Pharmaceutical Sciences (1980). The composition to be administered will, in any event, contain a quantity of the inhibitor and/or active compound(s) in a pharmaceutically effective amount for relief of the condition being treated when administered in accordance with the teachings of this invention. Generally, the inhibitors of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

Stability of the inhibitor can be further controlled by the composition and stereochemistry of the backbone and side chains of the polymer. For polypeptide polymers, D-isomers are generally resistant to endogenous proteases, and therefore have longer half-lives in serum and within cells. D-polypeptide polymers are therefore appropriate when longer duration of action is desired. L-polypeptide polymers have shorter half-lives due to their susceptibility to proteases, and are therefore chosen to impart shorter acting effects. This allows side-effects to be averted more readily by withdrawing therapy as soon as side-effects are observed. Polypeptides comprising mixtures of D and L-residues have intermediate stabilities. Homo-D-polymers are generally preferred.

The invention also relates to recombinant vectors incorporating DNA segments having sequences encoding chimeric polypeptides. For the purposes of the invention, the term chimeric polypeptide is defined as including any polypeptide where at least a portion of an inhibitor is coupled to a peptide containing a cleavage site. The coupling is achieved in a manner which provides for a functional transcribing and translating of the DNA segment and message derived from it, respectively. Such a peptide provides by its inclusion in the chimeric construct a site within the resulting chimeric polypeptide which may be cleaved in a manner to inactivate the intact inhibitor. A method of producing an inhibitor (polypeptide) is disclosed herein as well. The method comprises producing a recombinant host cell, which is capable of expressing the polypeptide. Of particular interest will be evaluation of candidate substances capable of determining the ability of the polypeptide to inhibit the undesirable activity of the candidate substance. The oligopeptides, peptide subunits and peptide derivatives (also termed peptides) of the present invention can be synthesized from their constituent amino acids by conventional peptide synthesis techniques, preferably by solid-phase technology. The peptides are then purified by reverse-phase high performance liquid chromatography (HPLC). A method of administration of an inhibitor is disclosed herein as well. The method comprises administration of the inhibitor alone or in combination with an active agent into a vertebrate, an animal, preferably a human. The invention can be used to target delivery of different antibodies, cytokines such as IL-2, GM-CSF, TNF, TRAIL, IFN and other molecules.

In preferred embodiment of this invention, the inhibitor is constructed by recombinant DNA techniques known to those skilled in the art and then selected for an optimal activity. The selection can be performed in vivo or in vitro. Selection techniques like DNA mutagenesis, phage display, virus replication, cell selection, FACS, and the like are contemplated. Since several molecules have been studied at a crystallographic level, the exact point of peptide insertion may be guided by an analysis of the spatial relationship of various amino acid residues. The X-ray crystal structure of a different antibodies, diabodies, receptors etc. have been determined enabling to those skilled in the art design of chimeric inhibitors of the instant invention with desired properties. An inhibitor containing a polypeptide sequence can be selected, mutagenized and reselected by phage display. In preferred embodiment of this invention, the inhibitor of the invention may be directly introduced into host organism or DNA encoding the inhibitor may be inserted into a plasmid, vector, virus, or viral vector, or other construct which is then inserted into a host cell. It is thus contemplated by the inventors that various changes may be made in the sequence of the peptides (or underlying DNA) without appreciable loss of their biological utility or activity. Site-specific mutagenesis is a technique useful in the preparation of second generation proteins, or biologically functional equivalent proteins or peptides, derived from the sequences thereof, through specific mutagenesis of the underlying DNA. Another aspect of this invention, is to provide host cell in which the inhibitor gene containing all or part of the nucleic acid sequences of interest can be propagated. The host cells containing the inhibitor of this invention include but are not limited to procaryotic cells, eukaryotic cells, vertebrates such as mice, monkey and humans. The host cells may be used to produce the inhibitor. In another aspect of this invention, vectors carrying the gene for the inhibitor of this invention may be used to transfer nucleic acid of interest for therapeutical purposes into humans or other vertebrate animals preferably mammals in need of therapy. The DNA, plasmids, viruses, or vectors carrying the gene for the inhibitor of this invention may be administered to animal or individual in need of a therapy in a variety of ways. The cells expressing the polypeptide may be administered or implanted in the organism or individual in need of therapy. A vector can also be introduced into a cell either ex vivo or in vivo. The host cells may be from virtually any species. In one embodiment the host cells are taken from the individual in need of a therapy. Examples of such cells include, but are not limited to stem cells, hematopoietic stem cells, tumor cells, and T cells. In another embodiment the cells are from a different individual or different species. Means of administering the host cells expressing the inhibitor, containing virus or vector encoding the inhibitor of the invention include but are not limited to, intravenous, intramuscular, intralesional, subcutaneous or intraperitoneal injection or implantation.

Viruses from host cells which release the inhibitor into supernatant fluid may be administered by administering the supernatant fluid or the host cells. The purified form of the virus or vector can be administered to the vertebrate in need of treatment alone or in the form of a pharmaceutical composition. Gene therapy may be also accomplished by inserting the nucleic acid sequences encoding the inhibitor of interest into the virus or vector and then introducing the virus or vector into the cell or organism. The infected host cell will express the desired polypeptide. Examples of diseases that might be suitable for a therapy using the instant invention include but are not limited to viral diseases, neurological disorders, cancer, or autoimmune diseases. In yet another aspect of the invention, the recombinant virus or vector encoding the inhibitor can be used to generate transgenic animal carrying the inhibitor in at least one cell. It may be introduced into an animal at an embryonic stage. Examples of the animals into which the inhibitor can be introduced include, but are not limited to non-human primates, dogs, cats, cows, sheep, horses, mice, rats or other rodents. Such animals may be used, but are not limited to use as biological models for study of diseases, evaluation of diagnostic or therapeutic methods for disease or vaccines or to generate a vaccine. It is further aspect of the invention to use the recombinant viruses or vectors encoding the inhibitor to deliver inhibitors, for instance, as vaccines, as cancer vaccines which include, but are not limited to transfer of the protein, virus or vector encoding the inhibitor to the tumor cells ex vivo and then after irradiating administer them back to the individual. If the individual is already afflicted with the disease the vaccine can be administered in conjunction with other therapeutic treatments. One skilled in the art will know the parameters to determine the proper way to make DNA constructs, to determine correct DNA, peptide or protein concentration to be administered. The therapy may be administered as often as necessary. The preventive and therapeutic methods described herein may be used alone or in conjunction with additional therapy known to those skilled in the art for the treatment of a given disease or condition.

All references cited herein are incorporated by reference in their entirety.

The following examples are intended to illustrate but not limit the present invention.

EXAMPLES

In light of the present disclosure and the general level of skill in the art, those of skill will appreciate that the following examples are intended to be exemplary only and that numerous changes, modifications and alterations can be employed without departing from the spirit and scope of the invention.

Example 1

TNFR-2 ECD Dimer with MMP Cleavage Site

A dimer of extra cellular domains (ECD) of human tumor necrosis factor receptor 2 (TNFR-2) is constructed. The N terminus ECD has the TNFR-2 leader sequence and the ECDs are separated by glycine linker that contains a Xho I-Sph I cassette with MMP cleavage site. The dimer is constructed by overlapping PCR using TNFR-2 cDNA as a template and primers which encode the glycine linker, the restriction sites, and the protease cleavage site. The TNFR-2 ECD MMP dimer construct is digested by Nco I and Bam HI, purified and cloned into similarly cut plasmid MFG. The 293 cells grown in D-MEM medium are transfected with the plasmids together with pSVNeo in 20:1 ratio using standard calcium phosphate transfection method. G418 resistant cells are cloned by serial dilutions and 18 independent stable transfectants are assayed for TNFR expression. The clones are grown in the presence of G418 (400 ug/ml) to about 80% confluency. The G418 medium is removed from the plates and replaced with serum free medium. After 48 h the medium is collected and concentrated by centrifugation on Centricon 30 spin columns. The supernatants are separated on 10% SDS-PAGE, blotted onto PVDF membrane, probed using human TNFR-specific monoclonal antibody, and visualized using HRP-labeled anti-mouse antibody and the ECL detection system. Clones with the highest TNFR expression are used in subsequent experiments. Efficiency and specificity of MMP-2 protease cleavage for the MMP-containing TNF-R dimer is determined. Accessibility of the MMP cleavage site to the MMP protease is demonstrated by treatment of the purified TNF-R with activated gelatinase A (MMP-2, Boehringer). The TNF-R is incubated with 10 U/ml of gelatinase A for 6 hours at 37° C. MMP cleavage products are separated on SDS-PAGE and subjected to Western blot analysis Efficiency of MMP cleavage is determined using two-fold dilutions of gelatinase A. The cleavage products resemble the TNF-R monomer. Monomeric purified human TNF-R (Sigma) is used as a molecular weight standard. The predicted molecular weight of the dimer is about 55 kDa. Negative controls are enterokinase, and mock treatment. The affinity of the MMP-containing dimer for TNF is determined biochemically, using a TNF column (Sigma). There is a direct correlation between affinity and pH needed to elute the protein. TNF-R from culture supernatants is purified on TNF affinity column and eluted on pH gradient ranging from 100 mM sodium phosphate pH 7.5 to 100 mM citric acid pH 2.1 is used. Fractions of 0.5 ml are collected and ELISA is used to determine the TNF-R concentration. Western blot is used to visualize the eluted TNF-R.

The cleavage of the dimer in cell culture expressing MMP is tested. Concentrated serum-free medium containing TNF-R and TNF-R/MMP is applied to MMP-positive HT 1080 cells and to MMP negative A431 cells and incubated for 1 hour. The medium is removed from cells, concentrated on Centricon column, and subjected to Western blot to determine efficiency and specificity of the protease cleavage. MMP inhibitors and MMP-neutralizing antibody (Biodesign) are used to establish that cleavage is mediated by MMP. The MMP activity that associates with MMP-expressing cell line HT 1080 is determined using 2,4 dinitrophenol-peptide (Bachem) and correlated to the activity of purified MMP-2 (Boehringer). HT 1080 cells are grown to semiconfluency, washed twice, the peptide diluted in serum-free medium (20 μM) is added and incubated for 1 hour at 37° C. Substrate hydrolysis is determined by monitoring the increase in fluorescence emission at 346 nm using an excitation wavelength of 280 nm.

The concentrated medium containing TNF-R and TNF-R/MMP dimers is tested for protection against TNF cytotoxic activity using WEHI 164 clone 13 mouse fibrosarcoma cell line. The WEHI assay is used to measure the protective effect of the MMP-containing TNF-R dimer from TNF cytotoxic activity. The WEHI 164 cells are very sensitive to TNF and are routinely used to determine TNF toxicity. Concentration of the TNFR in the medium is determined using SDS-PAGE. Standard TNF cytotoxic curve from 0.1 pg/ml to 500 pg/ml is constructed.

Two-fold dilutions of supernatants from cells expressing various TNF-R dimers (concentrated on Centricon 30 spin columns) are assayed. The samples are preincubated with 100 pg/ml of purified human TNF (Sigma) for 1 hour at 37° C. and tested in triplicates in the WEHI assay for protection against TNF cytotoxicity. Concentrations of TNF-R dimers that inhibit the killing activity of 100 pg/ml of human TNF by 50% and 100% are determined. From these TNF-R concentrations the ratio of TNF-R dimer antagonist bound to TNF is calculated. The purified human TNF (Sigma) is preincubated with dilutions of the TNFR-2 proteins-containing medium or with fresh D-MEM medium, which is used as a control, for 1 h at 37° C. and the percentage of cell death is determined under a microscope. Undiluted TNFR-2 medium as well as its low dilutions effectively protect WEHI cells from TNF toxicity. The purified human TNFR monomer (Sigma) is ineffective in the protection assay. About 32 pg of TNF-R dimer is needed to inhibit the cytotoxic effect of 100 pg of TNF by 50%. The stoichiometric ratio is about 1:1. ELISA and Western blot are used to determine TNF-R concentrations. The purified human TNF-R (Sigma) is used as a control. The TNF-R/MMP dimer protects the sensitive cells from TNF toxicity in dose dependent manner and functions as TNF inhibitor in vitro.

To determine TNF-R dimer cleavage by proteases expressed by tumor cells, the cells expressing TNF R dimers are grown to semiconfluency. The culture medium is collected, concentrated on Centricon 30 column, and applied to cancer cells expressing MMP. MMP-positive HT 1080 cells, MMP negative A431 cells are used. The TNF-R-containing medium is incubated with the cancer cells for 0.5, 1, 2, 4 and 8 hours. Following the incubation, TNF-R cleavage products are separated on SDS PAGE and subject to Western blot analysis. Purified gelatinase A is used as positive control. The cancer cell lines expressing the protease inactivate the dimer. The TNF-R protection from TNF cytotoxicity on WEHI cells mixed with cancer cell lines expressing MMP is also tested. 100 pg of purified human TNF is preincubated with amount of TNF-R which protects WEHI cells by 75%. The TNF/TNF-R complex is tested on WEHI cells spiked with two fold dilutions of MMP-positive HT 1080 cells or MMP-negative A431 cells. The MMP expressed by the cancer cells cleaves TNF-R liberating TNF from the complex. The cleavage results in increase in TNF cytotoxicity.

Example 2

Antibody with Recognition Site for PSA Protease

Anti-IL-2 antibody gene is cloned from hybridoma cell line S4B6 using standard PCR techniques. A peptide HSSKLQ (SEQ ID NO: 17) is inserted to the hinge and Fc region of human IgG1 sequence. An overlapping PCR is used for the construction. The peptide is inserted into the IgG sequence in the same reading orientation to create a junction between the glutamine of the peptide and the aspartic acid 216 of IgG1 heavy chain. The final DNA construct is sequenced to confirm the correct primary structure. PSA cleavage efficiency of the antibody is tested in cell culture. Concentrated serum-free medium containing the PSA peptide-containing antibody is applied to PC-82 human prostate cancer cell line, which secretes high levels of enzymatically active PSA. The medium is incubated for 1 hour with the cells, concentrated on Centricon column, and subjected to Western blot by which the efficiency and specificity of the protease cleavage is determines. PSA-neutralizing antibody (Biodesign) is used to establish that cleavage is mediated by PSA and PSA-nonproducing TSU human prostate cancer cell line is used as negative control. The PSA activity that associates with PSA expressing cell line is determined and correlated to the activity of purified PSA. A small fluorescently tagged peptide substrate is used to determined PSA hydrolysis. PC-82 cells are grown to semiconfluency, washed twice, the peptide diluted in serum-free medium (20 μM) is added and incubated for 1 hour at 37° C. Substrate hydrolysis is determined by monitoring the increase in fluorescence emission at 346 nm using an excitation wavelength of 280 nm.

Treatment of the PSA peptide-containing antibody/IL-2 complex with varying amounts of PSA releases biologically active IL-2 in a dose-response manner. 50 ng/ml of IL-2 in complex with the antibody is incubated with two-fold dilutions of purified PSA for 30 min at 37° C. A column loaded with monoclonal anti-IgG antibody is washed and the PSA peptide-containing antibody is immobilized on the column in the presence of TBS buffer pH 7.0 containing 0.15M NaCl. The column is washed several times with TBS, loaded with excess of IL-2 and washed with TBS. The cytokine is eluted from the column by treatment with purified PSA. The column is incubated with 10 U/ml of the protease for 30 min at 37° C. followed by elution with TBS. The biological activity of the eluted IL-2 is tested in cell culture assay. IL-2 bioavailability is measured by a standard bioassay protocol using an IL-2-dependent T cell line, CTLL-2. Standard proliferation curve is constructed from IL-2 concentrations 0.1 ng/ml to 500 ng/ml. Recombinant IL-2 (50 ng/ml) complexed with increasing concentrations of the antibody is preincubated and IL-2 bioactivity is determined by proliferation of the CTLL-2 cells. Incubation with the antibody alone in the absence of IL-2 is a negative control. CTLL-2 cells (5×103) are incubated with an IL-2-containing sample in a volume of 180 μl for 24 h at 37° C. in 96-well microtiter plates. Then 3H thymidine (0.5 mCi/well) is added, and the incorporation of radiolabeled thymidine into DNA is determined after overnight incubation. IL-2 bioactivity is determined by measuring proliferation of the CTLL-2 cell line. The IL-2-dependent CTLL-2 cells are incubated with varying amounts of conditioned medium from PSA-positive PC-82 cells in the presence of the antibody/IL-2 complex. The induction of proliferation of the IL-2-dependent cells is determined as a dose-response curve of increasing concentration of PSA-containing medium. Medium from PSA-negative TSU human prostate cancer cell line is used as a control. PSA cleavage products are separated on SDS-PAGE and subjected to Western blot analysis. A treatment of the PSA peptide containing antibody/IL-2 complex with PSA produced by PSA-positive PC-82 human prostate cancer cell line liberates active IL-2 from the complex.

To ensure that proliferation is mediated by IL-2, cultures are also be performed in the presence of anti-IL-2R antibody (PC61). The anti-IL-2 antibody binds and neutralizes IL-2 in vitro. Administration of the antibody together with the cytokine suppresses IL-2 cytotoxic activity. The cancer-specific protease cleaves the antibody releasing active IL-2.

Example 3

Anti-EGFR Antibody Inhibitors

Anti-EGFR antibody inhibitor is constructed as a dimer peptide linked by polyglycine serine linker containing PSA cleavage site. Peptide dimer GDSFTHTPPLDPQFYSSNK (G4S)3GDSFTHTPPLDP (SEQ.ID.NO.: 110) is synthesized and HPLC purified. Peptide inhibitor is incubated with purified PSA (Chemicon) in 50 mM Tris, 100 mM NaCl (pH 7.0) at a 1:10 molar ratio for 6 hours at 37° C. Cleavage products are analyzed by gel filtration on a Superdex 200 HR 10/30 column using 50 mM sodium-phosphate buffer, pH 7.4 containing 150 mM NaCl and a flow rate of 30 mL/hour; absorbance is monitored at 280 nm. Ratio of uncleaved versus cleaved products is quantified. The exact cleavage ends are confirmed through C terminal/N-terminal sequencing of reaction products. Anti-PSA mAb and serine protease inhibitors are used as controls. Hybridoma expressing monoclonal anti-EGFR antibody is purified by adsorption on immobilized protein A. One hundred mL of cell culture supernatant is passed through a high-TRAP protein A (Pharmacia) at a flow rate of 1 mL/min. Bound IgG is eluted with 100 mM citric acid, pH 3. After pH neutralization with Tris, pH 9, the mAb is dialyzed against 150 mM NaCl. The eluted immunoglobulin is concentrated on Centricon 30 spin column. The concentrated antibody (5 mg/mL) in PBS is used in subsequent experiments. The protein concentration is determined with Bio-Rad assay. The purity of the final protein preparation is evaluated by sodium dodecyl sulfate-polyacrylamide gel electrophoresis (SDS-PAGE) using a 8% gel followed by Coomassie blue staining.

Effect of the anti-EGFR antibody/inhibitor complex on the growth of human tumor A431 cell proliferation is examined. This cell line has been shown to secrete TGF and to be growth-inhibited by the addition of an anti-EGFR antibody. 2×103 cells in 100 μL of serum-free DMEM medium is seeded in a 96-well plate. Antibody (50 ng/mL) with two-fold dilutions of the inhibitor (100 μL/well) is added in triplicate to the wells and the cultures are incubated at 37° C. for 5 days. The controls consist of either medium alone or medium containing a control antibody with dilutions of the inhibitor. After incubation, the medium is removed and cells fixed with 0.25% glutaraldehyde, washed in 0.9% NaCl, air-dried, and stained with crystal violet (Fisher Scientific) for 15 min at room temperature. After wash and air-dry, 100 of methanol is added to each well and the absorbance at 595 nm is determined. The percentage of growth inhibition is calculated as follows: Mean A 595 measured in medium only minus A 595 in the presence of the antibody/inhibitor complex divided by mean A 595 in the presence of medium only multiplied by 100. The calculated IC50 values indicate that the inhibitor inactivates the antibody in vitro. Antibody affinity for peptide monomer is about 1,000 fold lower than for the dimer. The effect of the anti-EGFR antibody/inhibitor complex on A431 cell proliferation in the presence of cell-secreted PSA is examined. A431 cells are seeded in serum-free medium containing two-fold dilutions of conditioned media from PC-82 cells, which contains high levels of enzymatically active PSA. The antibody/inhibitor complex (50 ng/mL) is added in triplicate to the wells and the cultures are incubated for 5 days. The controls consist of medium with antibody only, medium without the antibody/inhibitor complex, and medium with a control antibody. PSA can hydrolyze the inhibitor and activate the antibody in vitro.

Ten nude mice at the age of 8 weeks are injected subcutaneously with five million A431 cells or A431 cells secreting active PSA (A431/PSA), 10 mice are used as controls. Animals also receive intraperitoneal injections of 500 ug anti-EGFR antibody or antibody/inhibitor complex, injections continue every 3 days for 28 days. Tumors are measured twice a week with a caliper and the volume is calculated. After 30 days, antibody treated A431 group displays reduced tumor growth when compared to the group treated with irrelevant antibody. Antibody/inhibitor complex treated A431 group displays slightly reduced tumor growth when compared to the group treated with irrelevant antibody. Antibody treated A431/PSA group displays reduced tumor growth when compared to the group treated with irrelevant antibody, similar effect as seen in A431 group. About 300 ug of antibody/inhibitor complex is needed in A431/PSA group to achieve similar tumor growth inhibition effect as in A431/PSA group treated with 500 ug of anti-EGFR antibody. The inhibitor when administered together with the antibody improves the therapeutic effect of the antibody in animals bearing tumors. After two months, all control animals developed significant tumors, 50% of animals treated with the antibody developed significant tumor mass and only 30% of animals treated with the antibody/inhibitor complex developed significant tumors.

Example 4

Anti-HER2 Antibody Inhibitors with Recognition Site for PSA Protease

Anti-HER2 antibody inhibitor is constructed as a dimer peptide linked by polyglycine serine linker containing PSA cleavage site. Peptide GYKDPPFCVAPLDPQFYSSNK (G4S)3GYKDPPFCVAPLDP (SEQ.ID.NO.: 111) is synthesized using solid phase chemistry and Applied Biosystems Peptide synthesizer, according to methods well known in the art. Peptides are purified using reverse phase HPLC columns, and their structures are confirmed using amino acid analysis and mass spectrometry. In the ELISA, 3.5 µg/ml of the HER2 receptor in PBS is adsorbed to microtiter plates overnight at 4° C. Plates are washed with PBS-0.05% Tween 20 to remove unbound antigen, blocked with 1% BSA in PBS-TW20 and incubated 1 hour at room temperature, washed as above and different concentrations of anti-HER2 antibody or different concentrations of anti-HER2 antibody in complex with the inhibitor are added to each well and incubated for 1 hour at room temperature. Plates are washed again and appropriate dilution of goat anti-mouse IgG coupled to horseradish peroxidase is added. The plates are incubated for 1 hour at room temperature and then washed as above. 0-phenylene diamine is added as substrate, incubated for 20 minutes at room temperature and then the reaction is stopped with 2.5 M H2SO4. The absorbance of each well is read at 492 nm. The binding of anti-HER2 antibody to the HER2 antigen is blocked by the inhibitor in dose dependent manner.

SK-BR-3 breast tumor cells are seeded at a density of 4×104 cells per well in 96-well microtiter plates and allowed to adhere for 2 hours. The cells are treated with different concentrations of anti-HER2 monoclonal antibody or different concentrations of anti-HER2 antibody in complex with the inhibitor or with irrelevant matched mAb at 0.05, 0.5 or 5.0 µg/ml and with 5,000 U/ml TNF for 4 hours. After a 72 hour incubation, the cell are stained with crystal violet dye to determine relative percent viability compared to cells treated with antibody in complex with the inhibitor or untreated control cells. The results show that incubation of cells overexpressing HER2 receptor with antibodies directed to the extracellular domain of the receptor induce sensitivity to the cytotoxic effects of TNF.

The antibody inhibit growth of cells that overexpress HER-2. When the cells overexpressing HER2 receptor are treated with antibodies in complex with the inhibitor no sensitivity to TNF is observed. The effect of anti-HER2 antibody/inhibitor complex on SKBr3 cell proliferation in the presence of PSA is determined. Cells are seeded in serum-free medium containing two-fold dilutions of conditioned media from PC-82 cells, which contains high levels of enzymatically active PSA. The antibody/inhibitor complex (50 ng/mL) is added in triplicate to the wells and the cultures are incubated for 5 days. The controls consist of medium with antibody only, and medium with a control antibody. The PSA activity in culture medium is measured and correlated with cell proliferation. The results shows that PSA protease can degrade the inhibitor and activate the antibody in vitro.

I claim:

1. A method of site specific activation of an antibody comprising administration of an inhibitor which is deactivatable by a protease produced by a target cell comprising:
   (a) a first moiety that binds, inhibits, suppresses, neutralizes, or decreases activity of said antibody wherein said first moiety is operably linked to
   (b) a second moiety comprising a polypeptide specifically cleavable by said protease produced by said target cell, wherein said first and second moieties are not attached in nature and wherein specific cleavage of said second moiety causes reduction of binding, inhibiting, suppressing, or neutralizing activity of said inhibitor and restoration of activity of said antibody;
   said inhibitor is administered alone or together with said antibody such that the activity of said antibody is reduced until it reaches said target cell producing said protease wherein the inhibitor is cleaved by said protease and activity of said antibody is restored.

2. The method of claim 1, wherein said first moiety comprises a polypeptide.

3. The method of claim 2, wherein the polypeptide is selected from the group consisting of a peptide, and a cyclic peptide.

4. The method of claim 1, wherein said first moiety comprises a polypeptide that binds, inhibits, suppresses, neutralizes, or decreases activity of a monoclonal antibody, a bispecific antibody, and a single chain antibody.

5. The method of claim 1, wherein said inhibitor is selected from the group consisting of a monoclonal antibody inhibitor, a bispecific antibody inhibitor, and a single chain antibody inhibitor or a combination thereof.

6. The method of claim 1, wherein said antibody is selected from the group consisting of a monoclonal antibody, a bispecific antibody and a single chain antibody or a combination thereof.

7. The method of claim 1, wherein said first and second moieties are connected by a peptide or a chemical linker.

8. The method of claim 1, wherein said first and said second moieties are connected by a peptide comprising a polyglycine serine linker.

9. The method of claim 1, wherein said second moiety is a polypeptide which comprises a sequence cleavable by two or more proteases.

10. The method of claim 1, wherein said second moiety is a polypeptide which comprises a sequence cleavable by a serine or cysteine protease.

11. The method of claim 1, wherein said second moiety is selected from the group consisting of SEQ ID NO:17, SEQ ID NO:19, SEQ ID NO:56, SEQ ID NO:57, and SEQ ID NO:60 or a combination thereof.

12. The method of claim 1, wherein said protease comprises a cysteine protease.

13. The method of claim 1, wherein said protease comprises a serine protease.

14. The method of claim 1, wherein said protease is selected from the group consisting of a prostate specific antigen, a matrix metalloproteinase, a plasminogen activator, a urokinase, a urokinase-type plasminogen activator, a tissue-type plasminogen activator, and a matriptase or a combination thereof.

15. The method of claim 1, wherein said protease is produced by a proliferating endothelial cell, a tumor cell, and a leukemia cell.

16. The method of claim 1, wherein said inhibitor further comprises a recognition domain that binds to an exterior surface of the targeted cell, or an extracellular matrix.

17. The method of claim 16, wherein said recognition domain binds to a proliferating endothelial cell, a tumor cell, and a leukemia cell.

18. The method of claim 16, wherein said recognition domain comprises an antibody.

19. The method of claim 16, wherein said recognition domain is selected from the group consisting of a monoclonal antibody, a bispecific antibody, and a single chain antibody or a combination thereof.

20. The method of claim 1, wherein said target cell comprises a tumor cell.

21. The method of claim 1, wherein said administration to a vertebrate results in a desired site specific activation of said antibody.

22. A method of site specific activation of a monoclonal antibody, a bispecific antibody and a single chain antibody or a combination thereof comprising administration of an inhibitor which is deactivatable by a reagent produced by a target cell comprising:

(a) a first moiety that binds, inhibits, suppresses, neutralizes, or decreases activity of said monoclonal antibody, bispecific antibody and single chain antibody or a combination thereof wherein said first moiety is operably linked to (b) a second moiety comprising a polypeptide specifically cleavable by said reagent comprising a protease produced by said target cell, wherein said first and second moieties are not attached in nature and wherein specific cleavage of said second moiety causes reduction of binding, inhibiting, suppressing, or neutralizing activity of said inhibitor and restoration of activity of said monoclonal antibody, bispecific antibody and single chain antibody or a combination thereof;

said inhibitor is administered alone or together with said monoclonal antibody, bispecific antibody and single chain antibody or a combination thereof such that the activity of said monoclonal antibody, bispecific antibody and single chain antibody or a combination thereof is reduced until it reaches said target cell producing said reagent wherein the inhibitor is cleaved by said reagent and activity of said monoclonal antibody, bispecific antibody and single chain antibody or a combination thereof is restored.

\* \* \* \* \*

SEQUENCE LISTING

```
<160> NUMBER OF SEQ ID NOS: 113

<210> SEQ ID NO 1
<211> LENGTH: 7
<212> TYPE: PRT
<213> ORGANISM: Unknown
<220> FEATURE:
<223> OTHER INFORMATION: mammalian, peptide specifically cleavable
      by a reagent produced by a target cell

<400> SEQUENCE: 1

Ser Met Ser Ile Ala Arg Leu
1               5

<210> SEQ ID NO 2
<211> LENGTH: 13
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 2

Ser Lys Gly Ser Phe Ser Ile Gln Tyr Thr Tyr His Val
1               5                   10

<210> SEQ ID NO 3
<211> LENGTH: 13
<212> TYPE: PRT
```

```
<213> ORGANISM: Unknown
<220> FEATURE:
<223> OTHER INFORMATION: mammalian, peptide specifically cleavable by
      a reagent produced by a target cell

<400> SEQUENCE: 3

His Leu Gly Gly Ser Gln Gln Leu Leu His Asn Lys Gln
1               5                   10

<210> SEQ ID NO 4
<211> LENGTH: 14
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 4

Ser Lys Gly Lys Gly Thr Ser Ser Gln Tyr Ser Asn Thr Glu
1               5                   10

<210> SEQ ID NO 5
<211> LENGTH: 8
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 5

Asp Arg Val Tyr Ile His Pro Phe
1               5

<210> SEQ ID NO 6
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 6

Val Val Cys Gly Glu Arg Gly Phe Phe Tyr Thr Pro
1               5                   10

<210> SEQ ID NO 7
<211> LENGTH: 7
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 7

Phe Phe Tyr Thr Pro Lys Ala
1               5

<210> SEQ ID NO 8
<211> LENGTH: 9
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 8

Lys Arg Arg Pro Val Lys Val Tyr Pro
1               5
```

<210> SEQ ID NO 9
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 9

Pro Val Gly Lys Lys Arg Arg Pro Val Lys Val Tyr
1               5                   10

<210> SEQ ID NO 10
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 10

Lys Pro Val Gly Lys Lys Arg Arg Pro Val Lys Val
1               5                   10

<210> SEQ ID NO 11
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 11

Gly Lys Pro Val Gly Lys Lys Arg Arg Pro Val Lys
1               5                   10

<210> SEQ ID NO 12
<211> LENGTH: 13
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 12

Thr Phe Ala Gly Asn Ala Val Arg Arg Ser Val Gly Gln
1               5                   10

<210> SEQ ID NO 13
<211> LENGTH: 6
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 13

Pro Leu Gly Leu Trp Ala
1               5

<210> SEQ ID NO 14
<211> LENGTH: 5
<212> TYPE: PRT
<213> ORGANISM: Unknown
<220> FEATURE:
<223> OTHER INFORMATION: mammalian, peptide specifically cleavable by
      a reagent produced by a target cell

```
<400> SEQUENCE: 14

Pro Leu Phe Tyr Ser
1               5

<210> SEQ ID NO 15
<211> LENGTH: 5
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 15

Pro Arg Thr Leu Thr
1               5

<210> SEQ ID NO 16
<211> LENGTH: 5
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 16

Pro Leu Arg Leu Ser
1               5

<210> SEQ ID NO 17
<211> LENGTH: 6
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 17

His Ser Ser Lys Leu Gln
1               5

<210> SEQ ID NO 18
<211> LENGTH: 6
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 18

Ser Gln Tyr Ser Asp Thr
1               5

<210> SEQ ID NO 19
<211> LENGTH: 7
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 19

Gln Phe Tyr Ser Ser Asn Lys
1               5

<210> SEQ ID NO 20
<211> LENGTH: 12
```

```
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 20

Val Ser Gln Asn Tyr Pro Ile Val Glu Asn Phe Asn
1               5                   10

<210> SEQ ID NO 21
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 21

Ser Lys Ala Arg Val Leu Ala Glu Ala Met Ser Asn
1               5                   10

<210> SEQ ID NO 22
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 22

Ser Ile Arg Lys Ile Leu Phe Leu Asp Gly Ile Asn
1               5                   10

<210> SEQ ID NO 23
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 23

Ser Ala Pro Gln Val Leu Pro Val Met His Pro Asn
1               5                   10

<210> SEQ ID NO 24
<211> LENGTH: 11
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 24

Ser Lys Thr Lys Val Leu Trp Gln Pro Lys Asn
1               5                   10

<210> SEQ ID NO 25
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 25

Ser Lys Thr Lys Val Leu Val Val Gln Pro Arg Asn
```

```
1               5                   10
```

```
<210> SEQ ID NO 26
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 26

Ser Thr Thr Gln Cys Phe Pro Ile Leu His Pro Asn
1               5                   10

<210> SEQ ID NO 27
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 27

Ser Gly Val Val Asn Ala Ser Cys Arg Leu Ala Asn
1               5                   10

<210> SEQ ID NO 28
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 28

Ser Ser Tyr Val Lys Ala Ser Val Ser Pro Glu Asn
1               5                   10

<210> SEQ ID NO 29
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 29

Ser Ala Leu Val Asn Ala Ser Ser Ala His Val Asn
1               5                   10

<210> SEQ ID NO 30
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 30

Ser Thr Tyr Leu Gln Ala Ser Glu Lys Phe Lys Asn
1               5                   10

<210> SEQ ID NO 31
<211> LENGTH: 12
<212> TYPE: PRT
<213> ORGANISM: Unknown
<220> FEATURE:
<223> OTHER INFORMATION: mammalian, peptide specifically cleavable by
```

```
                             -continued
    a reagent produced by a target cell

<400> SEQUENCE: 31

Ser Lys Ala Arg Val Leu Ala Glu Ala Met Ser Asn
1               5                   10

<210> SEQ ID NO 32
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 32

Ser Gln Asp Val Asn Ala Val Glu Ala Ser Ser Asn
1               5                   10

<210> SEQ ID NO 33
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 33

Ser Val Tyr Leu Gln Ala Ser Thr Gly Tyr Gly Asn
1               5                   10

<210> SEQ ID NO 34
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 34

Ser Lys Tyr Leu Gln Ala Asn Glu Val Ile Thr Asn
1               5                   10

<210> SEQ ID NO 35
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 35

Ser Glu Leu Arg Thr Gln Ser Phe Ser Asn Trp Asn
1               5                   10

<210> SEQ ID NO 36
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 36

Ser Glu Leu Trp Ser Gln Gly Ile Asp Asp Asp Asn
1               5                   10

<210> SEQ ID NO 37
```

```
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 37

Asp Leu Glu Val Val Thr Ser Thr Trp Val Phe Asn
1               5                   10

<210> SEQ ID NO 38
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 38

Asp Glu Met Glu Glu Cys Ala Ser His Leu Phe Asn
1               5                   10

<210> SEQ ID NO 39
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 39

Glu Asp Val Val Cys Cys Ser Met Ser Tyr Phe Asn
1               5                   10

<210> SEQ ID NO 40
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 40

Lys Gly Trp Arg Leu Leu Ala Pro Ile Thr Ala Tyr
1               5                   10

<210> SEQ ID NO 41
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 41

Ser Lys Pro Ala Lys Phe Phe Arg Leu Asn Phe Asn
1               5                   10

<210> SEQ ID NO 42
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 42
```

Ser Lys Pro Ile Glu Phe Phe Arg Leu Asn Phe Asn
1               5                   10

<210> SEQ ID NO 43
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 43

Ser Lys Pro Ala Glu Phe Phe Ala Leu Asn Phe Asn
1               5                   10

<210> SEQ ID NO 44
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 44

Ser Leu Leu Lys Ser Arg Met Val Pro Asn Phe Asn
1               5                   10

<210> SEQ ID NO 45
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 45

Ser Leu Leu Ile Ala Arg Arg Met Pro Asn Phe Asn
1               5                   10

<210> SEQ ID NO 46
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 46

Ser Lys Leu Val Gln Ala Ser Ala Ser Gly Val Asn
1               5                   10

<210> SEQ ID NO 47
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 47

Ser Ser Tyr Leu Lys Ala Ser Asp Ala Pro Asp Asn
1               5                   10

<210> SEQ ID NO 48
<211> LENGTH: 12
<212> TYPE: PRT
<213> ORGANISM: Unknown
<220> FEATURE:

<223> OTHER INFORMATION: mammalian, peptide specifically cleavable by
      a reagent produced by a target cell

<400> SEQUENCE: 48

Arg Pro Lys Pro Gln Gln Phe Phe Gly Leu Met Asn
1               5                   10

<210> SEQ ID NO 49
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 49

Ser Leu Arg Pro Leu Ala Leu Trp Arg Ser Phe Asn
1               5                   10

<210> SEQ ID NO 50
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 50

Ser Pro Gln Gly Ile Ala Gly Gln Arg Asn Phe Asn
1               5                   10

<210> SEQ ID NO 51
<211> LENGTH: 14
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 51

Asp Val Asp Glu Arg Asp Val Arg Gly Phe Ala Ser Phe Leu
1               5                   10

<210> SEQ ID NO 52
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 52

Ser Leu Pro Leu Gly Leu Trp Ala Pro Asn Phe Asn
1               5                   10

<210> SEQ ID NO 53
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 53

Ser Leu Leu Ile Phe Arg Ser Trp Ala Asn Phe Asn
1               5                   10

```
<210> SEQ ID NO 54
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 54

Ser Gly Val Val Ile Ala Thr Val Ile Val Ile Thr
1               5                   10

<210> SEQ ID NO 55
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 55

Ser Leu Gly Pro Gln Gly Ile Trp Gly Gln Phe Asn
1               5                   10

<210> SEQ ID NO 56
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 56

Lys Lys Ser Pro Gly Arg Val Val Gly Gly Ser Val
1               5                   10

<210> SEQ ID NO 57
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 57

Pro Gln Gly Leu Leu Gly Ala Pro Gly Ile Leu Gly
1               5                   10

<210> SEQ ID NO 58
<211> LENGTH: 31
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 58

His Gly Pro Glu Gly Leu Arg Val Gly Phe Tyr Glu Ser Asp Val Met
1               5                   10                  15

Gly Arg Gly His Ala Arg Leu Val His Val Glu Glu Pro His Thr
            20                  25                  30

<210> SEQ ID NO 59
<211> LENGTH: 12
<212> TYPE: PRT
<213> ORGANISM: Unknown
<220> FEATURE:
<223> OTHER INFORMATION: mammalian, peptide specifically cleavable by
```

-continued a reagent produced by a target cell

<400> SEQUENCE: 59

Gly Pro Gln Gly Leu Ala Gly Gln Arg Gly Ile Val
1               5                   10

<210> SEQ ID NO 60
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 60

Gly Gly Ser Gly Gln Arg Gly Arg Lys Ala Leu Glu
1               5                   10

<210> SEQ ID NO 61
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 61

Ser Leu Ser Ala Leu Leu Ser Ser Asp Ile Phe Asn
1               5                   10

<210> SEQ ID NO 62
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 62

Ser Leu Pro Arg Phe Lys Ile Ile Gly Gly Phe Asn
1               5                   10

<210> SEQ ID NO 63
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 63

Ser Leu Pro Arg Phe Lys Ile Ile Gly Gly Phe Asn
1               5                   10

<210> SEQ ID NO 64
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 64

Ser Leu Leu Gly Ile Ala Val Pro Gly Asn Phe Asn
1               5                   10

<210> SEQ ID NO 65

```
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 65

Phe Phe Lys Asn Ile Val Thr Pro Arg Thr Pro Pro
1               5                   10

<210> SEQ ID NO 66
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 66

Gln Val Val Gln Leu Gln Asn Tyr Asp Glu Glu Asp
1               5                   10

<210> SEQ ID NO 67
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 67

Leu Pro Ile Phe Gly Glu Ser Glu Asp Asn Asp Glu
1               5                   10

<210> SEQ ID NO 68
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 68

Gln Val Val Thr Gly Glu Ala Ile Ser Val Thr Met
1               5                   10

<210> SEQ ID NO 69
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 69

Ala Leu Glu Arg Thr Phe Leu Ser Phe Pro Thr Asn
1               5                   10

<210> SEQ ID NO 70
<211> LENGTH: 12
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 70
```

```
Lys Phe Gln Asp Met Leu Asn Ile Ser Gln His Gln
1               5                   10
```

<210> SEQ ID NO 71
<211> LENGTH: 2
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 71

```
Ala Ala
1
```

<210> SEQ ID NO 72
<211> LENGTH: 4
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 72

```
Ala Ala Pro Val
1
```

<210> SEQ ID NO 73
<211> LENGTH: 3
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 73

```
Ala Ala Met
1
```

<210> SEQ ID NO 74
<211> LENGTH: 4
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 74

```
Ala Ala Pro Phe
1
```

<210> SEQ ID NO 75
<211> LENGTH: 4
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 75

```
Ala Ala Pro Met
1
```

<210> SEQ ID NO 76
<211> LENGTH: 3
<212> TYPE: PRT
<213> ORGANISM: Unknown
<220> FEATURE:

```
<223> OTHER INFORMATION: mammalian, peptide specifically cleavable by
      a reagent produced by a target cell

<400> SEQUENCE: 76

Ala Ala Arg
1

<210> SEQ ID NO 77
<211> LENGTH: 4
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 77

Ser Ala Ala Arg
1

<210> SEQ ID NO 78
<211> LENGTH: 5
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 78

Ser Ser Ala Ala Arg
1               5

<210> SEQ ID NO 79
<211> LENGTH: 4
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 79

Ser Ala Ala Arg
1

<210> SEQ ID NO 80
<211> LENGTH: 3
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 80

Ala Ala Asp
1

<210> SEQ ID NO 81
<211> LENGTH: 4
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 81

Ser Ala Ala Asp
1
```

```
<210> SEQ ID NO 82
<211> LENGTH: 5
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 82

Ser Ser Ala Ala Asp
1               5

<210> SEQ ID NO 83
<211> LENGTH: 7
<212> TYPE: PRT
<213> ORGANISM: Unknown
<220> FEATURE:
<223> OTHER INFORMATION: mammalian, peptide specifically cleavable by
      a reagent produced by a target cell
<220> FEATURE:
<221> NAME/KEY: Variant
<222> LOCATION: 7
<223> OTHER INFORMATION: Xaa = any amino acid

<400> SEQUENCE: 83

Arg Pro Lys Pro Leu Ala Xaa
1               5

<210> SEQ ID NO 84
<211> LENGTH: 8
<212> TYPE: PRT
<213> ORGANISM: Unknown
<220> FEATURE:
<223> OTHER INFORMATION: mammalian, peptide specifically cleavable by
      a reagent produced by a target cell
<220> FEATURE:
<221> NAME/KEY: Variant
<222> LOCATION: 8
<223> OTHER INFORMATION: Xaa = any amino acid

<400> SEQUENCE: 84

Ser Arg Pro Lys Pro Leu Ala Xaa
1               5

<210> SEQ ID NO 85
<211> LENGTH: 9
<212> TYPE: PRT
<213> ORGANISM: Unknown
<220> FEATURE:
<223> OTHER INFORMATION: mammalian, peptide specifically cleavable by
      a reagent produced by a target cell
<220> FEATURE:
<221> NAME/KEY: Variant
<222> LOCATION: 9
<223> OTHER INFORMATION: Xaa = any amino acid

<400> SEQUENCE: 85

Ser Ser Arg Pro Lys Pro Leu Ala Xaa
1               5

<210> SEQ ID NO 86
<211> LENGTH: 7
<212> TYPE: PRT
<213> ORGANISM: Unknown
<220> FEATURE:
<223> OTHER INFORMATION: mammalian, peptide specifically cleavable by
      a reagent produced by a target cell
<220> FEATURE:
<221> NAME/KEY: Variant
<222> LOCATION: 2, 4, 7
<223> OTHER INFORMATION: Xaa = any amino acid
```

```
<400> SEQUENCE: 86

Pro Xaa Gly Xaa His Ala Xaa
1               5

<210> SEQ ID NO 87
<211> LENGTH: 7
<212> TYPE: PRT
<213> ORGANISM: Unknown
<220> FEATURE:
<223> OTHER INFORMATION: mammalian, peptide specifically cleavable by
      a reagent produced by a target cell
<220> FEATURE:
<221> NAME/KEY: Variant
<222> LOCATION: 5
<223> OTHER INFORMATION: Xaa = any amino acid

<400> SEQUENCE: 87

Pro Leu Gly Leu Xaa Ala Arg
1               5

<210> SEQ ID NO 88
<211> LENGTH: 4
<212> TYPE: PRT
<213> ORGANISM: Unknown
<220> FEATURE:
<223> OTHER INFORMATION: mammalian, peptide specifically cleavable by
      a reagent produced by a target cell
<220> FEATURE:
<221> NAME/KEY: Variant
<222> LOCATION: 2, 4
<223> OTHER INFORMATION: Xaa = any amino acid

<400> SEQUENCE: 88

Pro Xaa Gly Xaa
1

<210> SEQ ID NO 89
<211> LENGTH: 4
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 89

Pro Leu Gly Leu
1

<210> SEQ ID NO 90
<211> LENGTH: 3
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 90

Gly Pro Arg
1

<210> SEQ ID NO 91
<211> LENGTH: 3
<212> TYPE: PRT
<213> ORGANISM: Unknown
<220> FEATURE:
<223> OTHER INFORMATION: mammalian, peptide specifically cleavable by
      a reagent produced by a target cell
```

```
<400> SEQUENCE: 91

Leu Pro Arg
1

<210> SEQ ID NO 92
<211> LENGTH: 3
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 92

Glu Gly Arg
1

<210> SEQ ID NO 93
<211> LENGTH: 5
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 93

Gly Pro Gln Gly Ile
1               5

<210> SEQ ID NO 94
<211> LENGTH: 7
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 94

Asn Lys Ile Ser Tyr Gln Ser
1               5

<210> SEQ ID NO 95
<211> LENGTH: 6
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 95

Lys Ile Ser Tyr Gln Ser
1               5

<210> SEQ ID NO 96
<211> LENGTH: 19
<212> TYPE: PRT
<213> ORGANISM: Unknown
<220> FEATURE:
<223> OTHER INFORMATION: mammalian, peptide specifically cleavable by
      a reagent produced by a target cell
<220> FEATURE:
<221> NAME/KEY: Variant
<222> LOCATION: 12
<223> OTHER INFORMATION: Xaa = any amino acid

<400> SEQUENCE: 96

Gly Glu Asn Gly Val Gln Lys Asp Val Ser Gln Xaa Ser Ile Tyr Ser
1               5                   10                  15
```

Gln Thr Glu

<210> SEQ ID NO 97
<211> LENGTH: 15
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 97

Gly Lys Gly Ile Ser Ser Gln Tyr Ser Asn Thr Glu Glu Arg Leu
1               5                   10                  15

<210> SEQ ID NO 98
<211> LENGTH: 7
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 98

Asn Lys Ile Ser Tyr Tyr Ser
1               5

<210> SEQ ID NO 99
<211> LENGTH: 7
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 99

Asn Lys Ala Ser Tyr Gln Ser
1               5

<210> SEQ ID NO 100
<211> LENGTH: 5
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 100

Ser Tyr Gln Ser Ser
1               5

<210> SEQ ID NO 101
<211> LENGTH: 5
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 101

Arg Tyr Gln Ser Ser
1               5

<210> SEQ ID NO 102
<211> LENGTH: 8
<212> TYPE: PRT
<213> ORGANISM: Unknown
<220> FEATURE:
<223> OTHER INFORMATION: mammalian, peptide specifically cleavable by a reagent produced by a target cell

<400> SEQUENCE: 102

Asn Lys Ile Ser Tyr Gln Ser Ala
1               5

<210> SEQ ID NO 103
<211> LENGTH: 8
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 103

Ala Asn Lys Ile Ser Tyr Tyr Ser
1               5

<210> SEQ ID NO 104
<211> LENGTH: 8
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 104

Ala Asn Lys Ala Ser Tyr Gln Ser
1               5

<210> SEQ ID NO 105
<211> LENGTH: 6
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 105

Ser Tyr Gln Ser Ser Thr
1               5

<210> SEQ ID NO 106
<211> LENGTH: 6
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 106

Ser Tyr Gln Ser Ser Ser
1               5

<210> SEQ ID NO 107
<211> LENGTH: 6
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 107

Lys Tyr Gln Ser Ser Ser
1               5

<210> SEQ ID NO 108

```
<211> LENGTH: 6
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 108

Arg Tyr Gln Ser Ser Ser
1               5

<210> SEQ ID NO 109
<211> LENGTH: 6
<212> TYPE: PRT
<213> ORGANISM: Unknown
<220> FEATURE:
<223> OTHER INFORMATION: mammalian, peptide specifically cleavable by
      a reagent produced by a target cell

<400> SEQUENCE: 109

Ser Tyr Gln Ser Ser Leu
1               5

<210> SEQ ID NO 110
<211> LENGTH: 46
<212> TYPE: PRT
<213> ORGANISM: Artificial Sequence
<220> FEATURE:
<223> OTHER INFORMATION: Peptide dimer linked by polyglycine serine
      linker containing PSA cleavage site specifically cleavable by PSA

<400> SEQUENCE: 110

Gly Asp Ser Phe Thr His Thr Pro Pro Leu Asp Pro Gln Phe Tyr Ser
1               5                   10                  15

Ser Asn Lys Gly Gly Gly Gly Ser Gly Gly Gly Gly Ser Gly Gly Gly
            20                  25                  30

Gly Ser Gly Asp Ser Phe Thr His Thr Pro Pro Leu Asp Pro
        35                  40                  45

<210> SEQ ID NO 111
<211> LENGTH: 50
<212> TYPE: PRT
<213> ORGANISM: Artificial Sequence
<220> FEATURE:
<223> OTHER INFORMATION: Peptide dimer linked by polyglycine serine
      linker containing PSA cleavage site specifically cleavable by PSA

<400> SEQUENCE: 111

Gly Tyr Lys Asp Pro Pro Phe Cys Val Ala Pro Leu Asp Pro Gln Phe
1               5                   10                  15

Tyr Ser Ser Asn Lys Gly Gly Gly Gly Ser Gly Gly Gly Gly Ser Gly
            20                  25                  30

Gly Gly Ser Gly Tyr Lys Asp Pro Pro Phe Cys Val Ala Pro Leu
        35                  40                  45

Asp Pro
    50

<210> SEQ ID NO 112
<211> LENGTH: 5
<212> TYPE: PRT
<213> ORGANISM: Artificial Sequence
<220> FEATURE:
<223> OTHER INFORMATION: Peptide polyglycine linker
<220> FEATURE:
<221> NAME/KEY: Variant
<222> LOCATION: 3
```

```
<223> OTHER INFORMATION: Xaa = any amino acid

<400> SEQUENCE: 112

Gly Gly Xaa Gly Gly
1               5

<210> SEQ ID NO 113
<211> LENGTH: 4
<212> TYPE: PRT
<213> ORGANISM: Unknown
<220> FEATURE:
<223> OTHER INFORMATION: Ednoplasmic retaining sequence

<400> SEQUENCE: 113

Lys Asp Glu Leu
1
```